US008562657B2

(12) United States Patent
Ferren et al.

(10) Patent No.: US 8,562,657 B2
(45) Date of Patent: Oct. 22, 2013

(54) PHOTOPATTERNING OF SKIN

(75) Inventors: Bran Ferren, Beverly Hills, CA (US); Muriel Y. Ishikawa, Livermore, CA (US); Edward K. Y. Jung, Bellevue, WA (US); Nathan P. Myhrvold, Median, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 921 days.

(21) Appl. No.: 12/005,709

(22) Filed: Dec. 28, 2007

(65) Prior Publication Data

US 2008/0145326 A1 Jun. 19, 2008

Related U.S. Application Data

(60) Division of application No. 11/143,116, filed on Jun. 2, 2005, and a continuation-in-part of application No. 11/073,361, filed on Mar. 4, 2005.

(51) Int. Cl.
*A61N 5/06* (2006.01)

(52) U.S. Cl.
USPC .................................. 607/88; 606/9; 128/898

(58) Field of Classification Search
None
See application file for complete search history.

(56) References Cited

U.S. PATENT DOCUMENTS

| 3,685,051 A | 8/1972 | Wells |
| 4,214,490 A | 7/1980 | Chizek |
| 4,880,001 A | 11/1989 | Weinberg |
| 4,898,192 A | 2/1990 | Cohen |
| 4,979,935 A | 12/1990 | Lindmayer |
| 5,071,417 A | 12/1991 | Sinofsky |
| 5,226,907 A | 7/1993 | Tankovich |
| 5,279,284 A | 1/1994 | Fenn |
| 5,425,728 A | 6/1995 | Tankovich |
| 5,436,115 A | 7/1995 | Mullis |
| 5,470,351 A | 11/1995 | Ross et al. |
| 5,497,227 A | 3/1996 | Takeuchi et al. |
| 5,501,680 A | 3/1996 | Kurtz et al. |
| 5,586,981 A | 12/1996 | Hu |
| 5,606,798 A | 3/1997 | Kelman |
| 5,630,811 A | 5/1997 | Miller |
| 5,665,382 A | 9/1997 | Grinstaff et al. |
| 5,684,573 A | 11/1997 | Khazaka et al. |
| 5,743,899 A | 4/1998 | Zinreich |
| 5,757,523 A | 5/1998 | Wood et al. |
| 5,760,407 A | 6/1998 | Margosiak et al. |
| 5,773,592 A | 6/1998 | Mills |
| 5,820,625 A | 10/1998 | Izawa et al. |
| 5,833,649 A | 11/1998 | Atef |

(Continued)

FOREIGN PATENT DOCUMENTS

| JP | 07223816 A | 8/1995 |
| WO | WO 00/62700 | 10/2000 |

OTHER PUBLICATIONS

U.S. Appl. No. 11/974,077, Ferren et al.
U.S. Appl. No. 11/217,111, Ferren et al.
U.S. Appl. No. 11/198,910, Ferren et al.
U.S. Appl. No. 11/175,984, Ferren et al.
U.S. Appl. No. 11/143,925, Ferren et al.
U.S. Appl. No. 11/143,116, Ferren et al.
U.S. Appl. No. 11/073,361, Ferren et al.
U.S. Appl. No. 11/072,698, Ferren et al.
U.S. Appl. No. 11/072,007, Ferren et al.
Anseth, Kristi S.; "New Directions in Photopolymerizable Biomaterials"; Department of Chemical Engineering and the Howard Hughes Medical Institute; pp. 1-43; University of Colorado at Boulder.

(Continued)

*Primary Examiner* — Bill Thomson
*Assistant Examiner* — Lynsey Crandall

(57) ABSTRACT

Methods and systems for treating skin for aesthetic or health purposes are described. According to various embodiments, photoresponsive materials and light are delivered in a controlled fashion to produce a patterned distribution of a material in the skin.

19 Claims, 25 Drawing Sheets

(56) References Cited

U.S. PATENT DOCUMENTS

| | | | |
|---|---|---|---|
| 5,846,080 A | 12/1998 | Schneider | |
| 5,849,029 A | 12/1998 | Eckhouse et al. | |
| 5,853,407 A | 12/1998 | Miller | |
| 5,860,967 A | 1/1999 | Zavislan et al. | |
| 5,865,832 A | 2/1999 | Knopp et al. | |
| 5,871,480 A | 2/1999 | Tankovich | |
| 5,879,376 A | 3/1999 | Miller | |
| 5,914,255 A | 6/1999 | Grae | |
| 5,968,097 A | 10/1999 | Frechet et al. | |
| 5,990,193 A | 11/1999 | Russell et al. | |
| 5,998,588 A | 12/1999 | Hoffman et al. | |
| 6,013,122 A | 1/2000 | Klitzman et al. | |
| 6,022,361 A | 2/2000 | Epstein et al. | |
| 6,048,337 A | 4/2000 | Svedman | |
| 6,050,990 A * | 4/2000 | Tankovich et al. | 606/9 |
| 6,063,074 A | 5/2000 | Tankovich | |
| 6,074,382 A | 6/2000 | Asah et al. | |
| 6,090,790 A | 7/2000 | Eriksson | |
| 6,119,038 A | 9/2000 | Cook | |
| 6,152,917 A | 11/2000 | Tankovich | |
| 6,162,211 A | 12/2000 | Tankovich et al. | |
| 6,162,232 A | 12/2000 | Shadduck | |
| 6,168,590 B1 | 1/2001 | Neev | |
| 6,171,302 B1 | 1/2001 | Talpalriu et al. | |
| 6,190,315 B1 | 2/2001 | Kost et al. | |
| 6,192,890 B1 | 2/2001 | Levy et al. | |
| 6,215,893 B1 | 4/2001 | Leshem et al. | |
| 6,221,095 B1 | 4/2001 | Van Zuylen et al. | |
| 6,235,015 B1 | 5/2001 | Mead, III et al. | |
| 6,263,762 B1 | 7/2001 | Zeitler | |
| 6,267,724 B1 | 7/2001 | Taylor | |
| 6,267,771 B1 | 7/2001 | Tankovich et al. | |
| 6,273,884 B1 | 8/2001 | Altshuler et al. | |
| 6,277,128 B1 | 8/2001 | Muldner | |
| 6,306,119 B1 | 10/2001 | Weber et al. | |
| 6,306,128 B1 | 10/2001 | Waldman et al. | |
| 6,306,922 B1 | 10/2001 | Hubbell et al. | |
| 6,315,480 B1 | 11/2001 | Martel et al. | |
| 6,341,831 B1 | 1/2002 | Weber et al. | |
| 6,355,054 B1 * | 3/2002 | Neuberger | 607/89 |
| 6,358,242 B1 | 3/2002 | Cecchetti | |
| 6,358,516 B1 | 3/2002 | Harod | |
| 6,385,487 B1 | 5/2002 | Henley | |
| 6,387,103 B2 | 5/2002 | Shadduck | |
| 6,406,474 B1 | 6/2002 | Neuberger et al. | |
| 6,413,255 B1 | 7/2002 | Stern | |
| 6,416,747 B1 | 7/2002 | Laughlin | |
| 6,420,431 B1 | 7/2002 | Johnson | |
| 6,428,532 B1 | 8/2002 | Doukas et al. | |
| 6,456,001 B1 | 9/2002 | Iida et al. | |
| 6,457,585 B1 | 10/2002 | Huffer et al. | |
| 6,461,594 B1 | 10/2002 | Chaiken et al. | |
| 6,468,508 B1 | 10/2002 | Laughlin | |
| 6,470,891 B2 | 10/2002 | Carroll | |
| 6,474,343 B2 | 11/2002 | Laughlin | |
| 6,508,813 B1 | 1/2003 | Altshuler | |
| 6,511,475 B1 | 1/2003 | Altshuler et al. | |
| 6,514,243 B1 | 2/2003 | Eckhouse et al. | |
| 6,527,759 B1 | 3/2003 | Tachibana et al. | |
| 6,531,118 B1 | 3/2003 | Gonzalez et al. | |
| 6,533,774 B1 | 3/2003 | Ota | |
| 6,543,893 B2 | 4/2003 | Desormeaux | |
| 6,555,663 B1 | 4/2003 | Mills | |
| 6,565,532 B1 | 5/2003 | Yuzhakov et al. | |
| 6,569,157 B1 | 5/2003 | Shain et al. | |
| 6,584,359 B1 | 6/2003 | Motoi | |
| 6,602,274 B1 | 8/2003 | Chen | |
| 6,602,975 B2 | 8/2003 | Hubbell et al. | |
| 6,611,706 B2 | 8/2003 | Avrahami et al. | |
| 6,626,927 B1 | 9/2003 | Koplen | |
| 6,629,974 B2 | 10/2003 | Penny et al. | |
| 6,660,000 B2 | 12/2003 | Neuberger et al. | |
| 6,662,036 B2 | 12/2003 | Cosman | |
| 6,663,852 B2 | 12/2003 | Simon | |
| 6,672,341 B2 | 1/2004 | Bartholomew et al. | |
| 6,685,719 B2 | 2/2004 | Matera, Jr. | |
| 6,689,148 B2 | 2/2004 | Sawhney et al. | |
| 6,692,456 B1 | 2/2004 | Eppstein et al. | |
| 6,699,509 B1 | 3/2004 | Melinte et al. | |
| 6,717,102 B2 | 4/2004 | Neev et al. | |
| 6,723,750 B2 | 4/2004 | Voet | |
| 6,735,470 B2 | 5/2004 | Henley et al. | |
| 6,739,744 B2 | 5/2004 | Williams et al. | |
| 6,743,211 B1 | 6/2004 | Prausnitz et al. | |
| 6,743,222 B2 | 6/2004 | Durkin et al. | |
| 6,749,602 B2 | 6/2004 | Sierra et al. | |
| 6,758,845 B1 | 7/2004 | Weckwerth et al. | |
| 6,764,493 B1 | 7/2004 | Weber et al. | |
| 6,766,199 B2 | 7/2004 | Cook et al. | |
| 6,773,698 B1 | 8/2004 | Melinte et al. | |
| 6,790,205 B1 | 9/2004 | Yamazaki et al. | |
| 6,791,531 B1 | 9/2004 | Johnston et al. | |
| 6,800,122 B2 | 10/2004 | Anderson et al. | |
| 6,814,760 B2 | 11/2004 | Anderson et al. | |
| 6,818,018 B1 | 11/2004 | Sawhney | |
| 6,881,249 B2 | 4/2005 | Anderson et al. | |
| 6,997,923 B2 | 2/2006 | Anderson et al. | |
| 7,066,929 B1 | 6/2006 | Azar et al. | |
| 7,108,690 B1 | 9/2006 | Lefki et al. | |
| 7,131,446 B2 | 11/2006 | Tang et al. | |
| 7,135,033 B2 | 11/2006 | Altshuler et al. | |
| 7,170,034 B2 | 1/2007 | Shalev et al. | |
| 7,175,950 B2 | 2/2007 | Anderson et al. | |
| 7,179,253 B2 | 2/2007 | Graham et al. | |
| 7,204,832 B2 | 4/2007 | Altshuler et al. | |
| 7,220,427 B2 | 5/2007 | Jordan | |
| 7,250,047 B2 | 7/2007 | Anderson et al. | |
| 7,253,119 B2 | 8/2007 | Dutta | |
| 7,285,364 B2 | 10/2007 | Anderson et al. | |
| 7,300,666 B2 | 11/2007 | Jordan | |
| 7,316,820 B2 | 1/2008 | Jordan | |
| 7,344,587 B2 | 3/2008 | Khan et al. | |
| 7,435,524 B2 | 10/2008 | Anderson et al. | |
| 7,468,242 B2 | 12/2008 | Bellomo et al. | |
| 7,494,493 B2 | 2/2009 | Matsuura | |
| 7,699,917 B1 | 4/2010 | Pagnotta | |
| 7,713,265 B2 | 5/2010 | Dunki-Jacobs | |
| 7,734,321 B2 | 6/2010 | White | |
| 7,834,468 B2 | 11/2010 | Dutta | |
| 7,842,029 B2 | 11/2010 | Anderson et al. | |
| 7,870,951 B1 | 1/2011 | Orsi | |
| 7,886,742 B2 | 2/2011 | Haines et al. | |
| 7,905,854 B2 | 3/2011 | Hazut et al. | |
| 7,922,688 B2 | 4/2011 | Bodduluri et al. | |
| 7,962,192 B2 | 6/2011 | Bodduluri et al. | |
| 7,967,839 B2 | 6/2011 | Flock et al. | |
| 7,985,537 B2 | 7/2011 | Zheng et al. | |
| 7,988,199 B2 | 8/2011 | Welsh | |
| 8,002,753 B2 | 8/2011 | Krumme et al. | |
| 8,036,448 B2 | 10/2011 | Gildenberg | |
| 8,088,568 B2 | 1/2012 | Bellomo et al. | |
| 8,120,485 B2 | 2/2012 | Yang | |
| 8,142,990 B2 | 3/2012 | Bellomo et al. | |
| 8,175,718 B2 | 5/2012 | Wahlgren et al. | |
| 8,182,473 B2 | 5/2012 | Altshuler et al. | |
| 8,288,347 B2 | 10/2012 | Collette et al. | |
| 8,293,463 B2 | 10/2012 | Bellomo et al. | |
| 8,303,982 B2 | 11/2012 | Smith et al. | |
| 8,317,756 B2 | 11/2012 | Krumme et al. | |
| 8,343,132 B2 | 1/2013 | Heneveld et al. | |
| 8,371,306 B2 | 2/2013 | Haines et al. | |
| 8,393,249 B2 | 3/2013 | Godoy et al. | |
| 8,394,359 B1 | 3/2013 | O'Neil | |
| 8,420,077 B2 | 4/2013 | Altman et al. | |
| 2002/0087205 A1 | 7/2002 | Chen | |
| 2002/0091377 A1 | 7/2002 | Anderson et al. | |
| 2002/0107509 A1 | 8/2002 | Neuberger et al. | |
| 2002/0123746 A1 | 9/2002 | McDaniel | |
| 2002/0128696 A1 | 9/2002 | Pearl et al. | |
| 2002/0161357 A1 | 10/2002 | Anderson et al. | |
| 2002/0173780 A1 | 11/2002 | Altshuler et al. | |
| 2002/0173781 A1 | 11/2002 | Cense et al. | |
| 2002/0173782 A1 | 11/2002 | Cense et al. | |
| 2002/0193779 A1 | 12/2002 | Yamazaki et al. | |

(56) References Cited

U.S. PATENT DOCUMENTS

| | | |
|---|---|---|
| 2003/0018373 A1* | 1/2003 | Eckhardt et al. .............. 607/94 |
| 2003/0023235 A1 | 1/2003 | Cense et al. |
| 2003/0032950 A1 | 2/2003 | Altshuler et al. |
| 2003/0036751 A1 | 2/2003 | Anderson et al. |
| 2003/0060810 A1 | 3/2003 | Syrowicz et al. |
| 2003/0113540 A1 | 6/2003 | Anderson et al. |
| 2003/0159615 A1 | 8/2003 | Anderson et al. |
| 2003/0184831 A1 | 10/2003 | Lieberman |
| 2004/0015156 A1 | 1/2004 | Vasily |
| 2004/0024390 A1 | 2/2004 | Furumoto |
| 2004/0039379 A1 | 2/2004 | Viator et al. |
| 2004/0092913 A1 | 5/2004 | Hennings et al. |
| 2004/0133251 A1 | 7/2004 | Altshuler et al. |
| 2004/0228818 A1 | 11/2004 | Simon et al. |
| 2005/0137584 A1 | 6/2005 | Lemchen |
| 2005/0143719 A1 | 6/2005 | Sink |
| 2005/0234527 A1 | 10/2005 | Slatkine |
| 2005/0234528 A1 | 10/2005 | Tang et al. |
| 2005/0278002 A1 | 12/2005 | Eimerl et al. |
| 2006/0020260 A1 | 1/2006 | Dover et al. |
| 2006/0047330 A1 | 3/2006 | Whatcott et al. |
| 2006/0165657 A1 | 7/2006 | Bernasconi et al. |
| 2006/0178659 A1 | 8/2006 | Van Hal et al. |
| 2006/0206173 A1 | 9/2006 | Gertner et al. |
| 2006/0207978 A1 | 9/2006 | Rizun et al. |
| 2006/0276859 A1 | 12/2006 | Ferren et al. |
| 2006/0276860 A1 | 12/2006 | Ferren et al. |
| 2007/0027440 A1 | 2/2007 | Altshuler et al. |
| 2007/0032846 A1 | 2/2007 | Ferren et al. |
| 2007/0118098 A1 | 5/2007 | Tankovich |
| 2007/0160958 A1 | 7/2007 | Belikov et al. |
| 2007/0213791 A1 | 9/2007 | Van Hal et al. |
| 2008/0039827 A1 | 2/2008 | Ferren et al. |
| 2008/0269575 A1 | 10/2008 | Iddan |
| 2009/0076622 A1 | 3/2009 | Thompson et al. |

OTHER PUBLICATIONS

Baldacchini, Tommaso; Lafratta, Christopher N.; Farrer, Richard A.; Teich, Malvin C.; Saleh, Bahaa E.A.; Naughton, Michael J.; Fourkas, John T.; "Acrylic-based resin with favorable properties for three-dimensional two-photon polymerization"; Journal of Applied Physics; Jun. 1, 2004; pp. 6072-6076; vol. 95, No. 11; bearing dates of Dec. 16, 2003 and Mar. 8, 2004; American Institute of Physics.

Bozkurt, Alper; Onaral, Banu; "Safety assessment of near infrared light emitting diodes for diffuse optical measurements"; BioMedical Engineering OnLine; bearing a date of Oct. 6, 2004 and 1999-2004; pp. 1-11; vol. 3; BioMed Central Ltd; located at: http://www.biomedical-engineering-online.com/content/3/1/9; printed on Oct. 6, 2004.

Carlson, Peter; "Brand Xed, When Those Tattoos Really Get Under the Skin, It's Time for the Laser"; bearing a date of Oct. 5, 2005; pp. 1-5; C01; located at http://www.washingtonpost.com/wp-dyn/content/article/2005/10/04/AR2005100401740.html; The Washington Post Company.

Carmody, Pascal; "Photodynamic Therapy"; The Photodynamic Treatment Center; pp. 1-4; located at: http://www.gamma.ru/technica/articles-1/photodynamic_therapy.htm; printed on May 25, 2005.

Choi, Dong Hoon; Ban, Si Young; Kim, Jae Hong; "Stability of Photochromism in New Bifunctional Copolymers Containing Spiropyran and Chalcone Moiety in the Side Chain"; Bull. Korean Chem. Soc.; 2003; pp. 441-445; vol. 24, No. 4.

"Creme Based Body Products"; p. 1; located at: http://www.glowshop.com/en-gb/dpet_41.html; printed on May 9, 2005.

Dierickx, Christine C., M.D.; "Laser Hair Removal: Scientific Principles and Practical Aspects"; bearing a date of 2002; pp. 1-8; Lumenis.

"Glow-in-the-Dark Make-up"; p. 1; located http://www.glowshop.com/en-gb/dept_181.html; printed on May 9, 2005.

"Hair density"; keratin.com; pp. 1-4; located at: http://www.keratin.com/aa/aa014.shtml; printed on Jan. 18, 2005.

Hoekstra, Djoerd; "Hyaluronan-Modified Surfaces for Medical Devices"; Medical Device & Diagnostic Industry Magazine; Feb. 1999; bearing dates of 1999 and 2002; pp. 1-9; located at: http://www.devicelink.com/mddi/archive/99/02/005.html; printed on May 27, 2005.

Hunter, Ian W.; Brenan, Colin J.H.; Sebern, Elizabeth L.; "Design and Characterization of a Laser-based Instrument to Treat Hemangiomas Using Spectroscopic Feedback: The "Smart Scalpel""; MIT Home Automation and Healthcare Consortium; bearing a date of Oct. 1, 1999; Progress Report No. 2-4; pp. 1-16.

"Invisible Fluorescent Skin Stamp Inks"; Tri-Tech Inc.; bearing a date of Jul. 22, 2004; p. 1; located at: http://www.tritechusa.com/theft/skin_stamp.htm; printed on May 9, 2005.

Lach, Elliot M.D.; "Dermatology and Plastic Surgery"; pp. 126-133; located at: Absten, Gregory T., BSc, MBA; "Laser Medicine and Surgery"; bearing dates of 1996, 1999 and 2000; pp. 1-2; located at: http://www.lasertraining.org/fundamen.htm; printed on Nov. 4, 2004.

"More About Laser Hair Removal"; ShoreLaser center; bearing a date of Feb. 23, 2004; pp. 1-8; located at: http://www.shorelaser.com/LaserHairDet.html; printed on Jan. 21, 2005.

Nakayama, Y; Furumoto, A; Kidoaki, S; Matsuda, T; "Photocontrol of cell adhesion and proliferation by a photoinduced cationic polymer surface."; NCBI: Photochem Photobiol; bearing dates of May 2003 and May 16, 2005; pp. 1-2; vol. 77 (5); located at: http://www.ncbi.nlm.nih.gov/entrez/query.fcgi?cmd=Retrieve&db=pubmed&dopt=Abstract&list_uids=12812288&itool=iconabstr&query_hl=l; printed on May 31, 2005.

"Needleless Injection Device Developed"; Doctor's Guide to Medical & Other News; bearing dates of Dec. 18, 1997, 1998 and 1999; Doctor's Guide to the Internet; pp. 1-2; located at: http://www.docguide.com/dg.nsf/PrintPrint/C25BF2A7E04D079B85256571004F4D89; printed on Sep. 8, 2004.

Owens, Shelby, CME; "Photobiology of the Skin"; consumerbeware.com; bearing dates of 1998-2002; pp. 1-7; located at: http://www.consumerbeware.com/integumen2.htm; printed on Oct. 6, 2004.

Owens, Shelby, CME; "Photobiology of the Skin"; consumerbeware.com; bearing a dates of 1998-2002; pp. 1-4; located at: http://www.consumerbeware.com/integumen.htm; printed on Oct. 11, 2004.

"PenJet® Intellectual Property"; PenJet® Needle-Less, Disposable Jet Injectors; Penjet® Corporation; pp. 1; located at: http://www.penjet.com/pages/patents.html; printed on Sep. 8, 2004.

"Photodynamic Therapy"; MEDLINE Abstract Collection; bearing dates of 2001 and Aug. 5, 2002; pp. 1-3; located at: http://www.medscape.com/viewarticle/438317_print; printed on May 25, 2005.

"PHOTOEPILATION: A comparative analysis of different light sources for better epilation efficacy"; pp. 1-7; located at : http://www.solarlaser.com/photoepilation_1_en.htm; printed on Oct. 6, 2004.

Pogue, Brian W.; Hasan,Tayyaba; "Targeting in Photodynamic Therapy and Photo-Imaging"; Optics & Photonics News; pp. 36-43; Aug. 2003; Optical Society of America.

Pope, Karl; "Comparative Monte Carlo Examination of Energy Penetration for Different Hair Removal Lasers"; Clinical Update; pp. 1-4; Jan. 2000; Candela Corporation.

"Researchers Use Laser to Build Micro-Structures on a Human Hair", Physorg.com; May 27, 2004; pp. 1-3; located at http://www.physorg.com/news4295.html; printed on Sep. 7, 2005.

Suthamjariya, Kittisak, MD; Taylor, Charles R. MD; "Photodynamic Therapy for the Dermatologist"; emedicine: Instant Access to the Minds of Medicine; bearing dates of Aug. 20, 2002 and 2005; pp. 1-10; located at: http://emedicine.com/derm/topic636.htm; printed on May 25, 2005.

Sy, Linda; "PDT: A bright old drug therapy"; Skin411 Digest; Mar. 2004; pp. 1-3; located at: http://www.lindasy.com/cgi-local/SoftCart.100.exe/skin411/411_mar04p2.html?L+scstore+mpdx9867ff719e71+1121170020; printed on May 27, 2005.

"UV Body Tattoos"; pp. 1-2; located at: http://www.glowshop.com/en-gb/dept_68.html; printed on May 9, 2005.

'Nano-tattoo' May Help Diabetics Track Their Blood Sugar; Chemistry/Analytical Chemistry; May 28, 2010; 2 pages; located at www.physorg.com/news194248207.html.

* cited by examiner

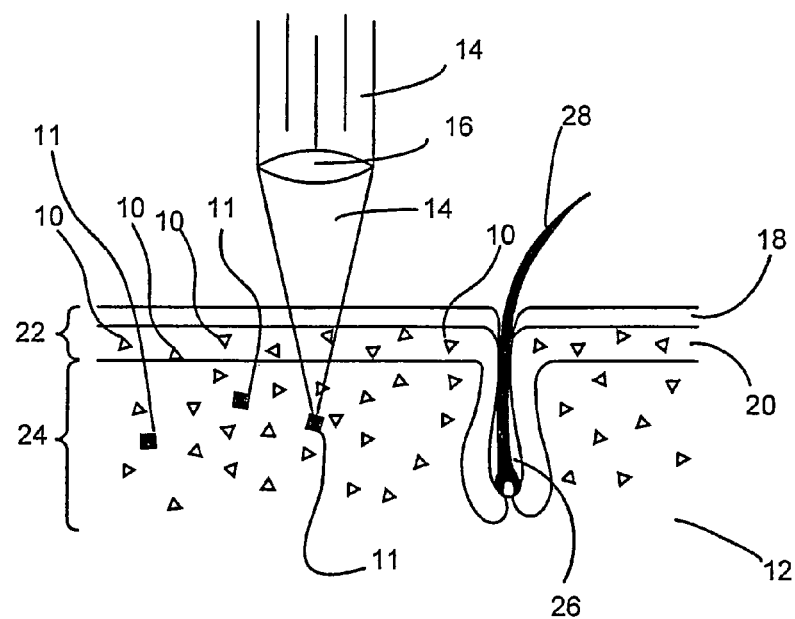
FIG. 1
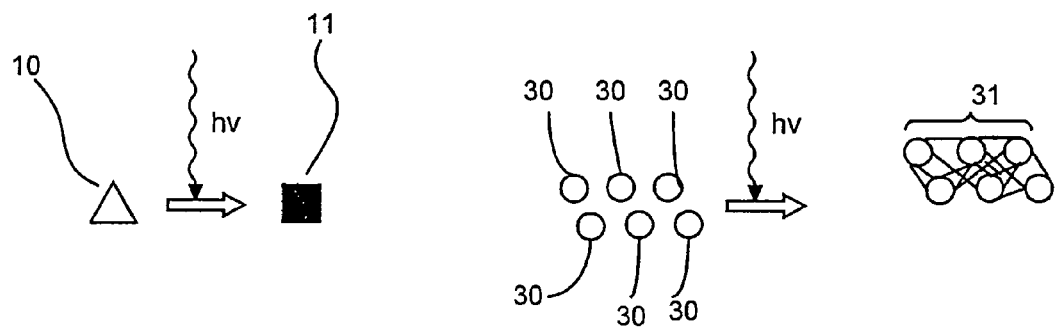
FIG. 2A
FIG. 2B

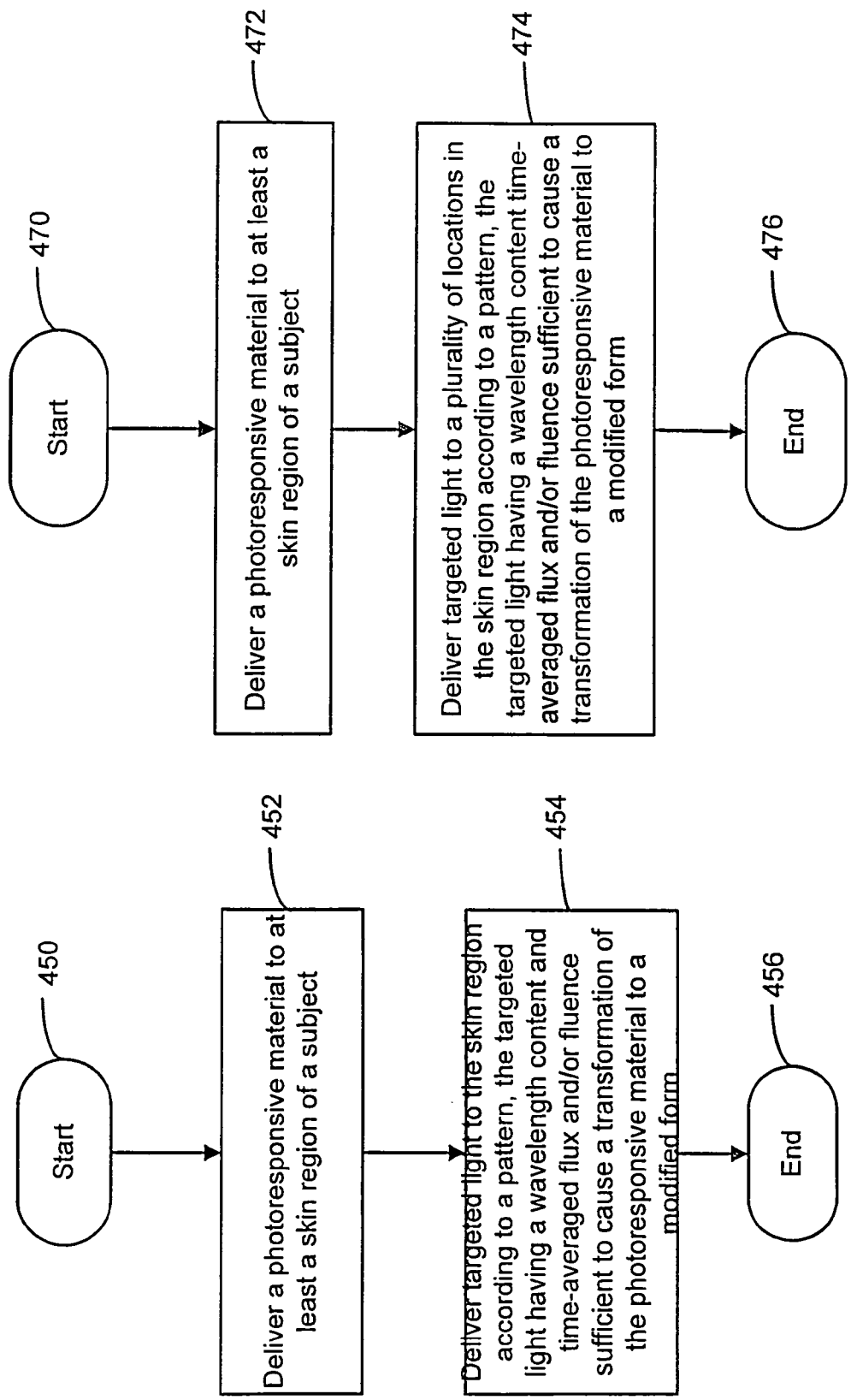

PHOTOPATTERNING OF SKIN

CROSS-REFERENCE TO RELATED APPLICATIONS

For purposes of the United States Patent Office (USPTO) extra-statutory requirements, the present application is a DIVISION application of U.S. patent application Ser. No. 11/143,116 titled PHOTOPATTERNING OF SKIN, naming BRAN FERREN, MURIEL Y. ISHIKAWA, EDWARD K. Y. JUNG, NATHAN P. MYHRVOLD, AND LOWELL L. WOOD, JR. as inventors, filed 2 Jun. 2005, which is co-pending, or is an application of which a co-pending application is entitled to the benefit of the filing date. The present application claims the benefit of the earliest available effective filing date(s) (i.e., claims earliest available priority dates for other than provisional patent applications or claims benefits under 35 USC §119(e) for provisional patent applications) for any and all applications to which patent application Ser. No. 11/143,116 claims the benefit of priority, including but not limited to U.S. patent application Ser. No. 11/073,361, titled METHOD AND SYSTEM FOR TEMPORARY HAIR REMOVAL, naming BRAN FERREN, MURIEL Y. ISHIKAWA, EDWARD K. Y. JUNG, NATHAN P. MYHRVOLD, CLARENCE T. TEGREENE, AND LOWELL L. WOOD, JR. as inventors, filed 4 Mar. 2005 as a continuation-in-part thereof. All subject matter of U.S. patent application Ser. No. 11/143,116 and of any and all applications from which it claims the benefit of the earliest available effective filing date(s) is incorporated herein by reference to the extent such subject matter is not inconsistent herewith.

The USPTO has issued new rules regarding Claims and Continuations, effective Nov. 1, 2007, 72 Fed. Reg.—21 Aug. 2007, available at: http://www.uspto.gov/web/offices/com/sol/notices/72fr46716.pdf; wherein 37 CFR 1.78(d)(1) states that the USPTO will refuse to enter any specific reference to a prior-filed application that fails to satisfy any of 37 CFR 1.78(d)(1)(i)-(vi). The applicant entity has provided above a specific reference to the application(s) from which priority is being claimed—as required by statute. Applicant entity understands that the statute is unambiguous in its specific reference language and does not require either a serial number or any characterization, such as "continuation" or "continuation-in-part" or "divisional," for claiming priority to U.S. patent applications. Notwithstanding the foregoing, the applicant entity has provided above a specific reference to the application(s) from which priority is being claimed that satisfies at least one of the extra-statutory requirements of 37 CFR 1.78(d)(1)(i)-(vi), but expressly points out that such designations are not to be construed in any way as any type of commentary and/or admission as to whether or not the present application contains any new matter in addition to the matter of its parent application(s). Further, any designation that the present application is a "division" should not be construed as an admission that the present application claims subject matter that is patentably distinct from claimed subject matter of its parent application.

TECHNICAL FIELD

The present application relates, in general, to the field of treating skin for aesthetic and/or health and/or other purposes. In particularly, this application relates to methods and systems for controlling the delivery of materials into or onto skin.

BACKGROUND

The introduction of various dyes or other pigmented materials into or onto the skin to in the form of cosmetics or tattoos is well known, as is the application of various biologically active compounds onto or into the skin surface for various medical-related purposes. In recent years, light-activated photodynamic therapy agents have been developed for the treatment of various skin problems, including skin cancers.

SUMMARY

According to various embodiments, methods are provided for forming patterned distributions of materials in the skin of a subject. A desired pattern may be formed by delivering a photoresponsive material to the skin and exposing the skin to light or other electromagnetic energy to cause a reaction or conversion of the photoresponsive material. In some embodiments, a photoresponsive material may be delivered into or onto the skin in a pattern. In some embodiments, patterned light may be delivered to the skin. One or both the photoresponsive material and light may be patterned in order to form a desired distribution of material. Materials distributed in or on the skin may have a variety of properties for aesthetic, cosmetic, functional, health, or medical purposes. Features of various embodiments will be apparent from the following detailed description and associated drawings.

BRIEF DESCRIPTION OF THE FIGURES

Features of the invention are set forth in the appended claims. The exemplary embodiments may best be understood by making reference to the following description taken in conjunction with the accompanying drawings. In the figures, like referenced numerals identify like elements.

FIG. 1 illustrates focusing of light in a skin region to produce modification of a photoresponsive material;

FIG. 2A illustrates transformation of a photoresponsive substance from a first form to a second form with exposure to light;

FIG. 2B illustrates cross-linking of a photoresponsive substance on exposure to light;

FIG. 12 is a flow diagram of a further method of forming a pattern in skin;

FIG. 13 is a flow diagram of a further method of forming a pattern in skin;

FIGS. 23A-22C illustrate steps of forming a patterned distribution of material in skin;

DETAILED DESCRIPTION

Figure 3A:
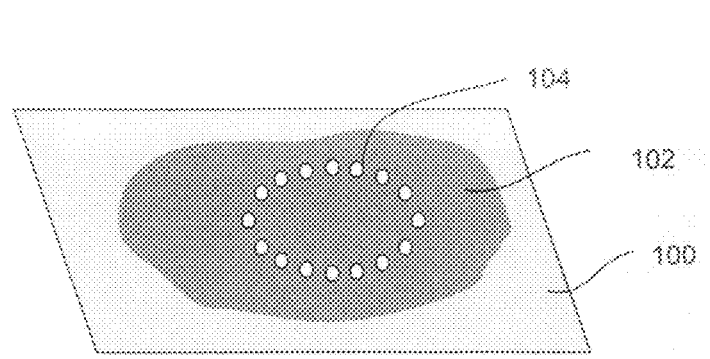
FIGS. 3A-3C illustrate photopatterning of skin by targeted application of light.

In the following detailed description, reference is made to the accompanying drawings, which form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims.

Throughout the specification and claims, the following terms take the meanings explicitly associated herein unless the context dictates otherwise. The meaning of "a", "an", and "the" include plural references. The meaning of "in" includes "in" and "on." A reference to the singular includes a reference to the plural unless otherwise stated or inconsistent with the disclosure herein.

According to various embodiments as disclosed herein, methods and systems are provided for forming patterned distributions of materials in or on skin. Patterned distributions of materials in skin may have various applications, including but not limited to aesthetic, cosmetic, functions, medical or health purposes. Patterned distributions of dyes, pigments, or other light absorbing, reflecting, or emitting materials, (or any other materials that may produce a visually or optically detectable effect) may be used for aesthetic, decorative, or cosmetic purposes (for example, as tattoos or permanent or semi-permanent cosmetics). Detectable markings, which may be detectable visually or optically, or by electrical, magnetic, acoustic, or various other detection methods, may have functional applications, as well, for example, marking the location of a surgical site on a patient, or for providing permanent or semi-permanent identifying markings, e.g., on pets, livestock, etc. Patterned distributions of materials having pharmaceutical activity may used to selectively treat various structures in or near the skin surface. Treatment targets may include skin lesions, including cancerous and precancerous skin lesions, moles, warts, and pimples. Treatment may also be applied to disorders of various skin structures, for example, capillaries, veins, sweat glands, and hair follicles. In other embodiments, patterned distributions of structural materials (e.g., materials that add strength, form, shape, bulk, resilience, or other desired structural or mechanical properties to skin, connective tissue, cartilage, and so forth) may be used for cosmetic or reconstructive surgery applications. In some cases, a few example of which are provided above, it may be desirable to form a pattern of material that remains in the skin permanently or semi-permanently. In other cases, e.g., if the patterned material is a biologically active compound intended to treat a specific medical problem, only transient presence of the patterned material may be desired.

FIG. 1 illustrates modification of a photoresponsive material in skin caused by delivery of light. In FIG. 1, molecules or particles of photoresponsive material 10 are distributed throughout skin region 12, and light 14 is targeted to a specific location by lens 16, where it produces a reaction or other modification of one or more molecules or particles of photoresponsive material 10 to produce modified form 11. Skin region 12 includes stratum corneum 18 and keratinocyte layer 20, which together form epidermis 22, and dermis 24. Also shown is hair follicle 26 and hair 28. Photoresponsive material 10 may be distributed in the form of molecules, clusters or aggregations of molecules, particles, gels, solutions, emulsions, suspensions, sprays, fluids, powders, among others. As used herein, the term photoresponsive material refers to a material (compound, element, composite material, etc.) that undergoes or participates in a reaction, interaction, transformation, modification, phase change, change in energetic state, etc.) to produce a reaction product, or modified form, indicated by reference number 11 in FIG. 1, having one or more different activities or properties than the original or 'unmodified' photoresponsive material. A "modification", as used herein may include chemical reactions, changes in energetic state, phase, conformation, associations, aggregations, formation of bonds or other interactions (e.g. molecular bonds, hydrogen bonds, van der Waals linkages, etc.), polymerization, cross linking, breaking of bonds, dissociation of associated molecules, atoms, ions, etc., oxidation or reduction reactions, formation of ions or free radicals, changes of 3-D molecular structure, being only examples. Photoresponsive material may be any material that is responsive or sensitive to light to change from a first state to a second state, by itself or in cooperation or reaction with other materials present. In some embodiments, a photoresponsive material may undergo a modification that results in a modification to a secondary material, in which it is the secondary material that produces an effect in the skin. In other embodiments, the photoreactive material may be employed as a light-specified 'mask' which then is used to control the exposure of skin not so 'masked' to subsequent processing. Photoresponsive material may include mixtures of materials that react or interact upon exposure to light. FIG. 2A depicts a change in conformation produced by exposure to light, in which photoresponsive material 10 is converted from a first state 10 to a second state 11. FIG. 2B depicts cross linking of multiple molecules 30 of photoresponsive material produced by exposure to light, to form crosslinked network 31. Conversion of a photoreactive material from an unreacted to a reacted form may include conversion from inactive to active form, from active to inactive form, from colored form to non-colored form, from a darker form to a lighter oner (or vice versa), from a more-scattering form to a less-scattering one (or vice versa), from a first color to a second color, or any combination of these. Conversion of a photoreactive material from an unreacted form to a reacted form may include a changes in the scattering or absorption properties of the photoreactive material for light of a given waveband.

Various methods of delivering photoresponsive material and light to a skin region may be used to produce a patterned distribution of a material in the skin region. One or the other or both of the photoresponsive material and the light may be delivered in a targeted fashion in order to produce a patterned distribution of material in the skin.

Figure 3B:
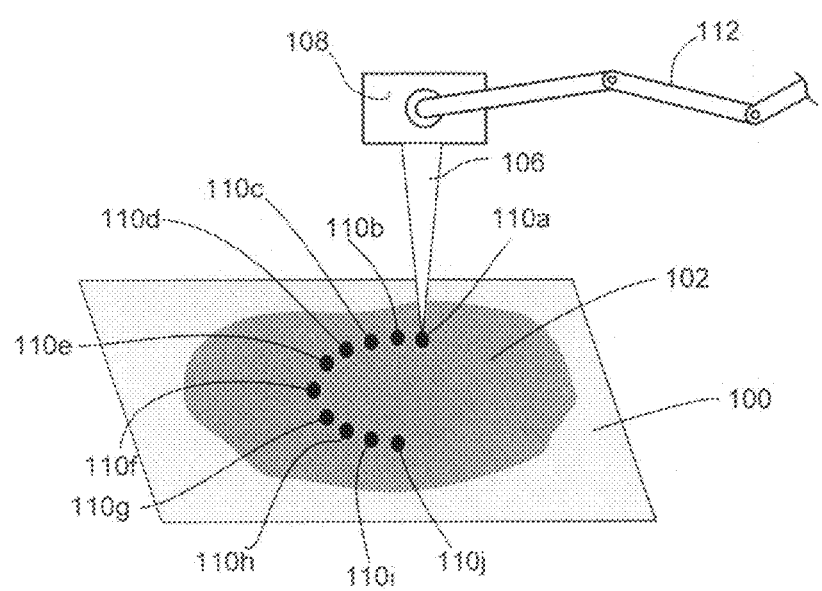
Figure 3C:
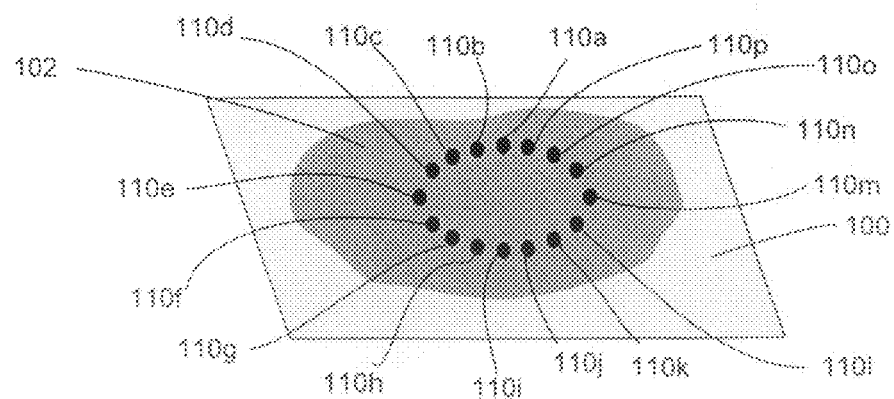

In some embodiments, a patterned distribution of a material in or on skin may be produced by delivering a photoresponsive material to at least a skin region of a subject in a relatively non-targeted fashion, and delivering targeted light to the skin region according to a pattern. The targeted light may have a wavelength content, time-averaged flux and/or fluence sufficient to cause a transformation of the photoresponsive material to a modified form. As illustrated in FIGS. 3A-3C, the method may include delivering targeted light to the skin region according to a pattern by delivering targeted light to a plurality of locations in the skin region according to a pattern. A patterned distribution of the modified form of the photoresponsive material may then be formed. This general approach is illustrated in FIG. 3A-3C. In FIG. 3A, a skin region 100 is illustrated. Photoresponsive material has been applied to a portion 102 of skin region 100. Multiple locations to which targeted light is to be delivered (represented by white circles 104) are depicted in FIG. 3A. Focused light 106 from light source 108 is delivered to location 110a, which is one of multiple locations 110a-110j within portion 102. FIG. 3B illustrates delivery of light 106 to location 110a, where photoresponsive material is converted to a modified form, indicated by a dark circle. FIG. 3B depicts multiple locations 110b-110j that have previously been exposed to light to cause modification of photoresponsive material. Light source 108 may be positioned with respect to skin region 108 by a linkage 112. FIG. 3C depicts a pattern of modified material at locations 110a-110o.

Figure 4A:
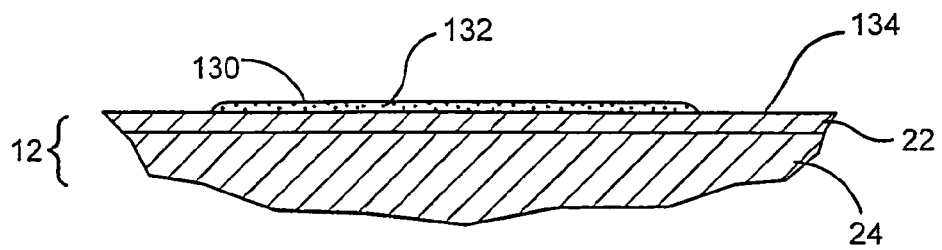
FIG. 4A illustrates topical application of a photoresponsive material.
Figure 4B:
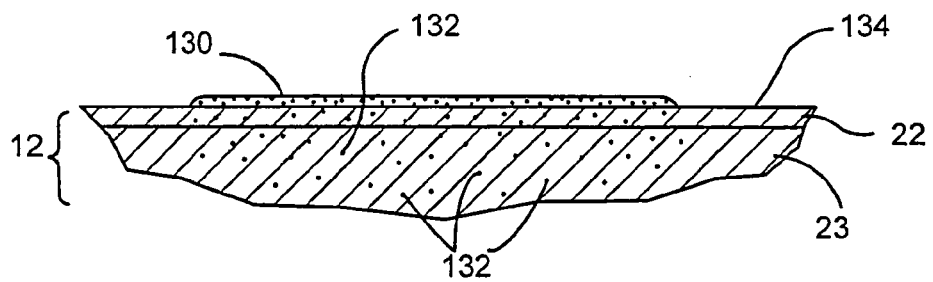
FIG. 4B illustrates diffusion of topically applied photoresponsive material into the skin.

Delivery of photoresponsive material in relatively non-targeted fashion may be accomplished by various methods, which may depend on various factors, including the type of photoresponsive material to be used, desired depth of delivery of the material in the skin, the size of the area in which a patterned distribution of material is to be produced. In some embodiments, photoresponsive material may be delivered to the skin topically. As illustrated in FIG. 4A, a carrier material 130 containing a photoresponsive material 132 may be placed on a skin surface 134. Photoresponsive material 132 may diffuse out of carrier material 130 and into skin 12, as shown in FIG. 4B. Skin 12 includes epidermis 22 and dermis 24. Diffusion of photoresponsive material 132 may be enhanced by electrophoresis or by the presence of solvent or 'carrier' chemicals such as DMSO or EDTA in certain embodiments (see, e.g., "Photodynamic Therapy", Medscape Dermatology 3(2), 2002, incorporated herein by reference. Photoresponsive material may be delivered to at least a skin region of a subject topically in various forms, including, for example, an aerosol, cream, emulsion, gel, liquid, vapor, gas, lotion, patch, or powder or combinations of these.

Figure 5A:
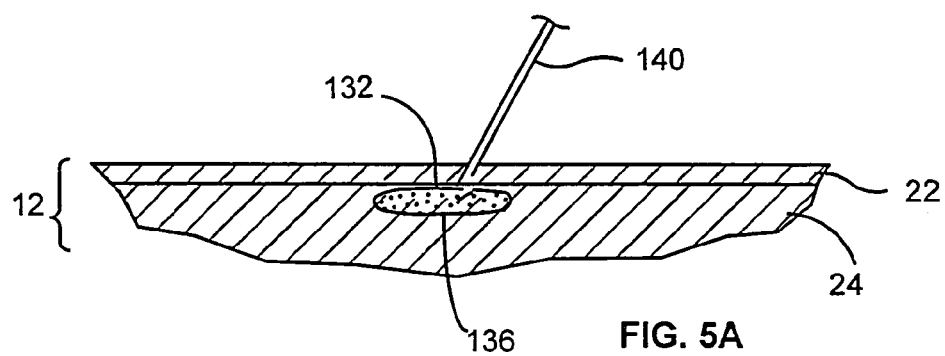
FIG. 5A illustrates hypodermal injection of photoresponsive material.
Figure 5B:
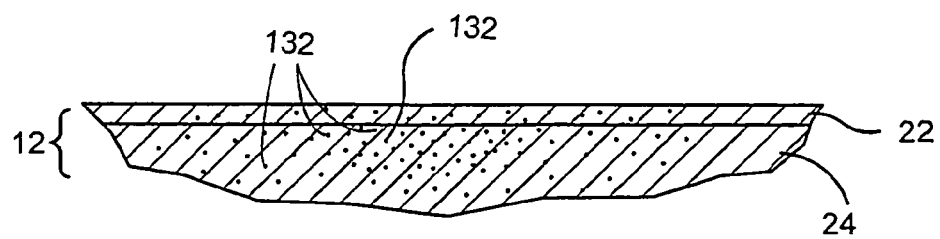
FIG. 5B illustrates diffusion of injected photoresponsive material.
Figure 6:
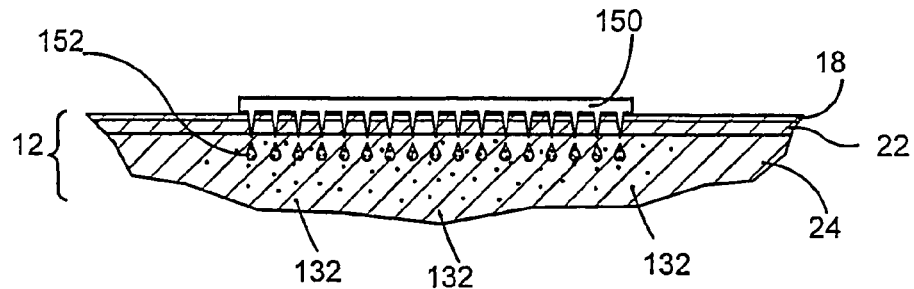
FIG. 6 illustrates injection of photoresponsive material into skin with a microneedle array.

In some cases, a general distribution of a photoresponsive material within a skin region may be obtained by injecting the photoresponsive material 132 into skin 12 with an hypodermic needle 140, as depicted in FIG. 5A. Photoresponsive material 132 may be in a liquid carrier solution 136, or in a suspension, an emulsion, or any other form suitable for delivery via a hypodermic needle. This approach may be suitable if the diffusion or dispersion of the photoresponsive material away from the injection site produces an acceptable (e.g., sufficiently uniform) distribution of photoresponsive material, as depicted in FIG. 5B, within an acceptable amount of time. Alternatively, photoresponsive material may be distributed into a skin region 12 with the use of a microneedle array 150, as depicted in FIG. 6. Photoresponsive material 132 may be injected below stratum corneum 18 of skin region 12 with the use of a microneedle array 150. As described in connection with the embodiment depicted in FIG. 5A, photoresponsive material to be delivered via microneedle array 150 may be carried in a carrier fluid 152 that is adapted for use with a microneedle array.

The distribution of photoresponsive material 132 that can be obtained within skin region 12 may depend on the combination of injection methodology and photoresponsive material used. For example, smaller molecules may diffuse or disperse more readily from the injection site than may larger molecules. In addition, the presence of certain functional groups may cause some photoresponsive materials to be taken up by certain tissues or cell types. Accordingly, photoresponsive materials may be selected or designed for use in combination with certain delivery mechanism and for preferential delivery to, retention by, or processing by certain tissues or cells. The design or selection of photoresponsive materials to have certain diffusion or selective uptake-or-retention-or-processing properties may be performed by a person of skill in the relevant art, for example, as described in Pogue and Hasan, "Targeting in Photodynamic Therapy and Photo-Imaging, Optics & Photonics News, August 2003, pp. 36-43, which is incorporated herein by reference.

Figure 7:
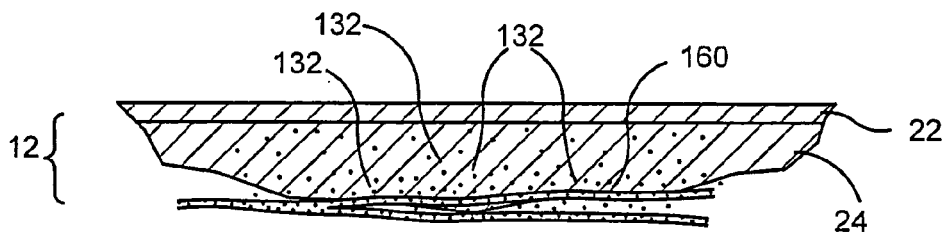
FIG. 7 depicts diffusion of photoresponsive material into skin from a capillary.

In some embodiments, a photoresponsive material may be delivered to at least a skin region of a subject by delivering the photoresponsive material to the subject systemically. For example, photoresponsive material may be delivered to the subject orally in an ingestible formulation, via an inhalant, via intravenous or other 'deep' injection modalities or via various other systemic routes. In some cases, a photoresponsive material may be delivered via injection, but subsequently carried throughout the body by the blood stream. As depicted in FIG. 7, a systemically delivered photoresponsive material 132 may be carried in the blood stream (e.g., in capillary 160) and diffuse out into the skin region of interest, which in this example is skin region 12. Depending on the particular photoresponsive material, it may distribute uniformly throughout the subject's body, or may distribute preferentially to certain regions, tissues, or cells of the body. In this, and other embodiments, the photoresponsive material may be attached to a carrier molecule compounded in various ways as known to those of skill in the arts of drug delivery, in order to produce a desired distribution of photoresponsive material within the subject's body.

Figure 8:
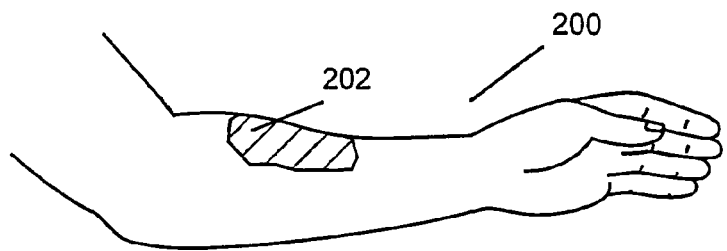
FIG. 8 depicts a skin region including a photoresponsive substance.
Figure 9:
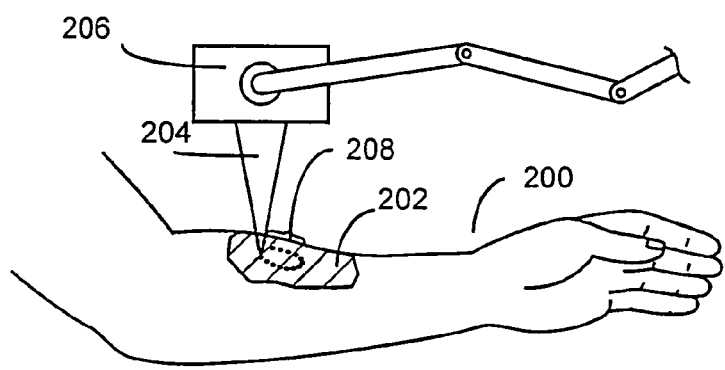
FIG. 9 depicts targeted application of light to a skin region including a photoresponsive substance.

FIG. 8 depicts the arm 200 of a subject, showing a skin region 202 in which a photoresponsive material is distributed. In this and other embodiments, photoresponsive material may be distributed only to the skin region of interest (skin region 202 in the present example), by, for example, topical application or local injection, or it may be distributed to a larger portion of the subject's body (up to and including the entire body), of which the region of interest is a part. In FIG. 9, patterned light 204 is delivered to skin region 202 from light source 206 to cause modification of the photoresponsive material to produce a patterned distribution 208 of the modified material in skin region 202.

Figure 10:
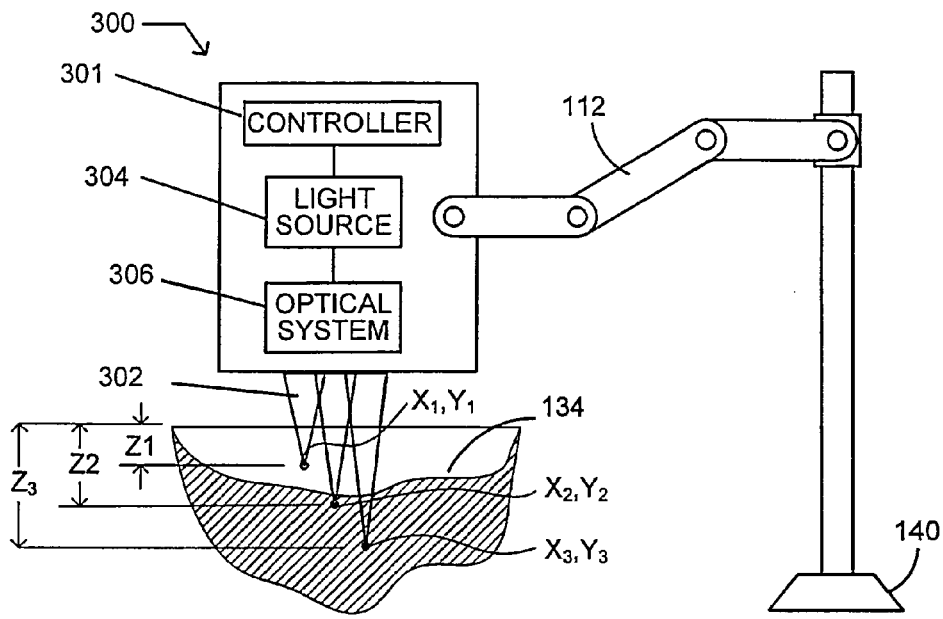
FIG. 10 depicts an embodiment of a system for controlled delivery of light to skin.

FIG. 10 provides a general illustration of a device 300 that may be used to produce a patterned distribution of light. Controller 301 controls the deliver of light 302 from light source 304 via optical system 306. Device 300 may be positioned by a mechanical linkage 112 supported by a base 140. Light 302 may be delivered at different x,y positions on the skin surface (e.g. $x_1$, $y_1$, $x_2$, $y_2$, $x_3$, and $y_3$ in FIG. 10), as well as at different depths or z positions (e.g. $z_1$, $z_2$, and $z_3$ in FIG. 10) below the skin surface 134. Each location may be characterized by an x coordinate and y coordinate in an effectively planar portion of the skin region. Similarly, each location may be characterized by z coordinate corresponding to the depth of the location below a surface of the skin region. In some applications, the z coordinate may be selected for each location such that a pattern is formed in the epidermis of the skin region. In other applications, the z coordinate may be selected for each location such that a pattern is formed in the dermis of the skin region, or even below the dermis.

Figure 11:
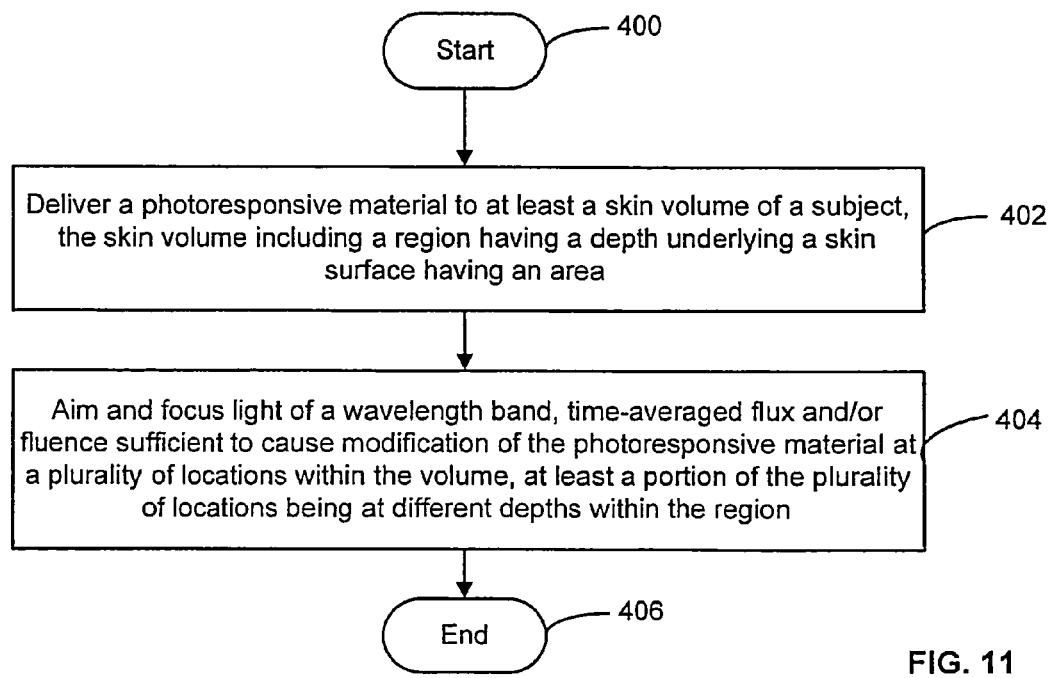
FIG. 11 is a flow diagram of a method of forming a pattern in a skin volume.

A method as depicted in FIG. 11 may be used for forming a pattern in a skin volume. At step 402, a photoresponsive material is delivered to at least a skin volume of a subject, the skin volume including a region having a depth underlying a skin surface having an area. At step 404, light of a wavelength band, time-averaged flux and/or fluence sufficient to cause modification of the photoresponsive material may be aimed and focused at a plurality of locations within the volume, with at least a portion of the plurality of locations being at different depths within the region.

FIG. 12 depicts steps of a method of forming a patterned distribution of material in skin, including delivering a photoresponsive material to at least a skin region of a subject at step 452 and delivering targeted light to the skin region according to a pattern, the targeted light having a wavelength content, time-averaged flux and/or fluence sufficient to cause a transformation of the photoresponsive material to a modified form, at step 454. FIG. 13 depicts a related method, which includes delivering a photoresponsive material to at least a skin region of a subject at step 472 and delivering targeted light to a plurality of locations in the skin region according to a pattern, the targeted light having a wavelength content, time-averaged flux and/or fluence sufficient to cause a transformation of the photoresponsive material to a modified form, in step 474.

Figure 14:
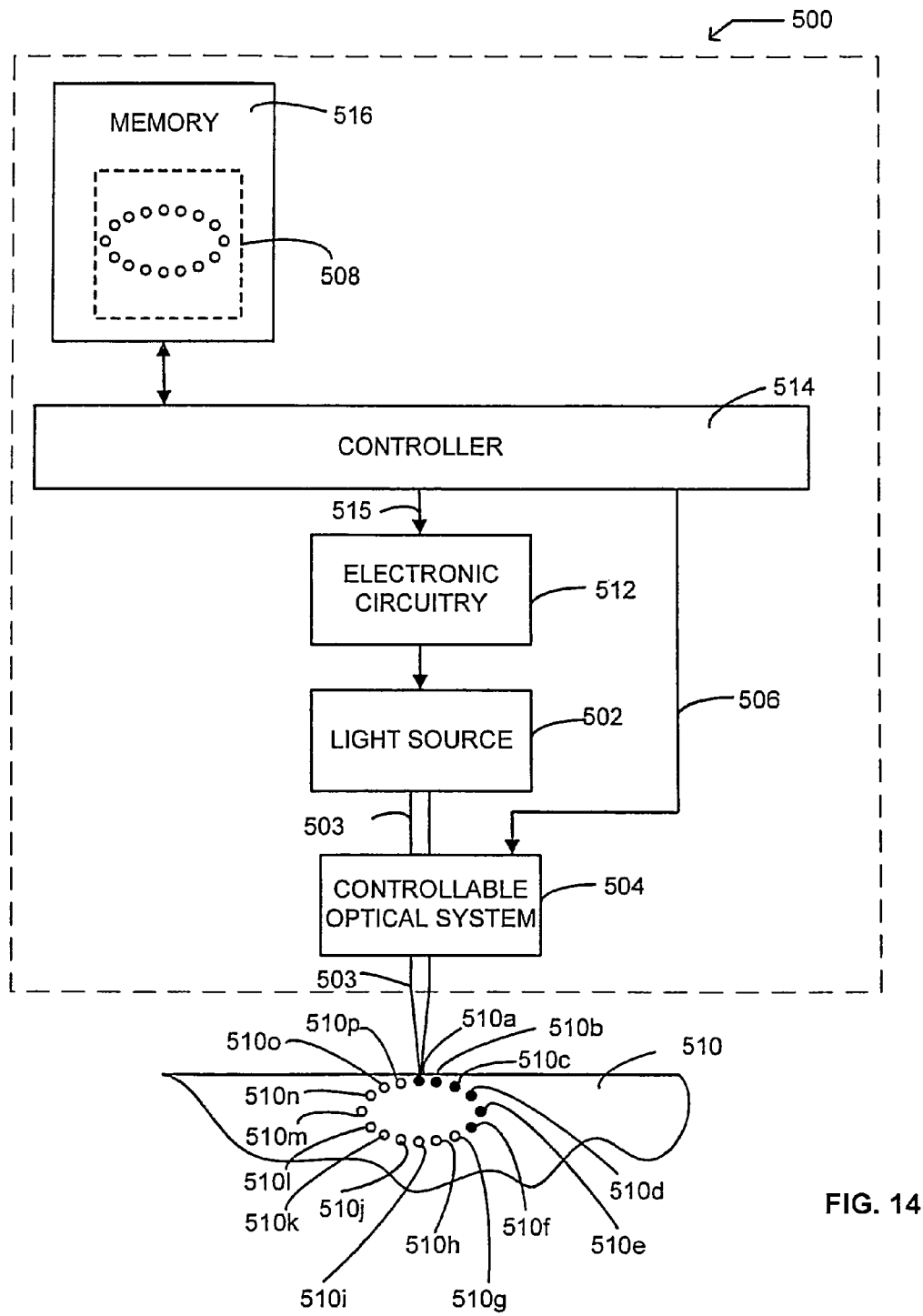
FIG. 14 is a block diagram of a system for targeted application of light to skin.

FIG. 14 is a block diagram of a system 500 for delivering patterned light. System 500 includes a light source 502 capable of producing light 503 of at least one defined wavelength band, and a controllable optical system 504. Controllable optical system 504 is configured to receive control signal 506 generated according to a pattern 508, and responsive to the control signal 506 to aim and focus light 503 from the light source 502 onto one or more selected skin locations of the plurality of skin locations 510a-510p according to pattern 508. Pattern 508 may represent a desired distribution of a material to a plurality of locations in or on skin region 510. System 500 may also include electronic circuitry 512 configured to limit the fluence of light 503 produced by the light source 502 to levels that are non-damaging or not significantly damaging to skin. Controller 514, which may be, for example, a microprocessor, may perform computations used to produce control signal 506 for controlling controllable optical system 504, and light source drive signal 515 for driving light production by light source 502. Electronic circuitry 512 may function to limit light source drive signal 515 to limit light generation to safe levels. In some embodiments, a system for delivering patterned light to skin may include a light source capable of producing light of at least one defined wavelength band, a controllable optical system, and electronic circuitry configured to limit the fluence of light produced by the light source to levels that are non-damaging or not significantly damaging to skin. The controllable optical system may be configured to receive a control signal generated according to a pattern representing a desired distribution of a material to a plurality of locations in or on a skin region, and responsive to the control signal to aim and focus light from the light source onto one or more selected skin locations of the plurality of skin locations according to the pattern. The system for delivering patterned light may also include an imaging device adapted for imaging a skin region containing at least a portion of the plurality of skin locations. In some embodiments, the system may include a device driver including one or more of hardware, software, or firmware for generating the control signal based upon pattern data stored in a machine readable medium. In some embodiments, the controllable optical system may include one or more deflectors configured to aim light from the light source, and the position of at least one of the one or more reflectors may be controllable to aim light toward at least one of the plurality of skin locations. In some embodiments, the controllable optical system may include a positioner adapted to adjust the position of the light source. Deflectors may include mirror-type reflectors and surface-acoustic wave (SAW) Bragg-type deflectors, as well as electrically-steered refractive elements.

Figure 15:
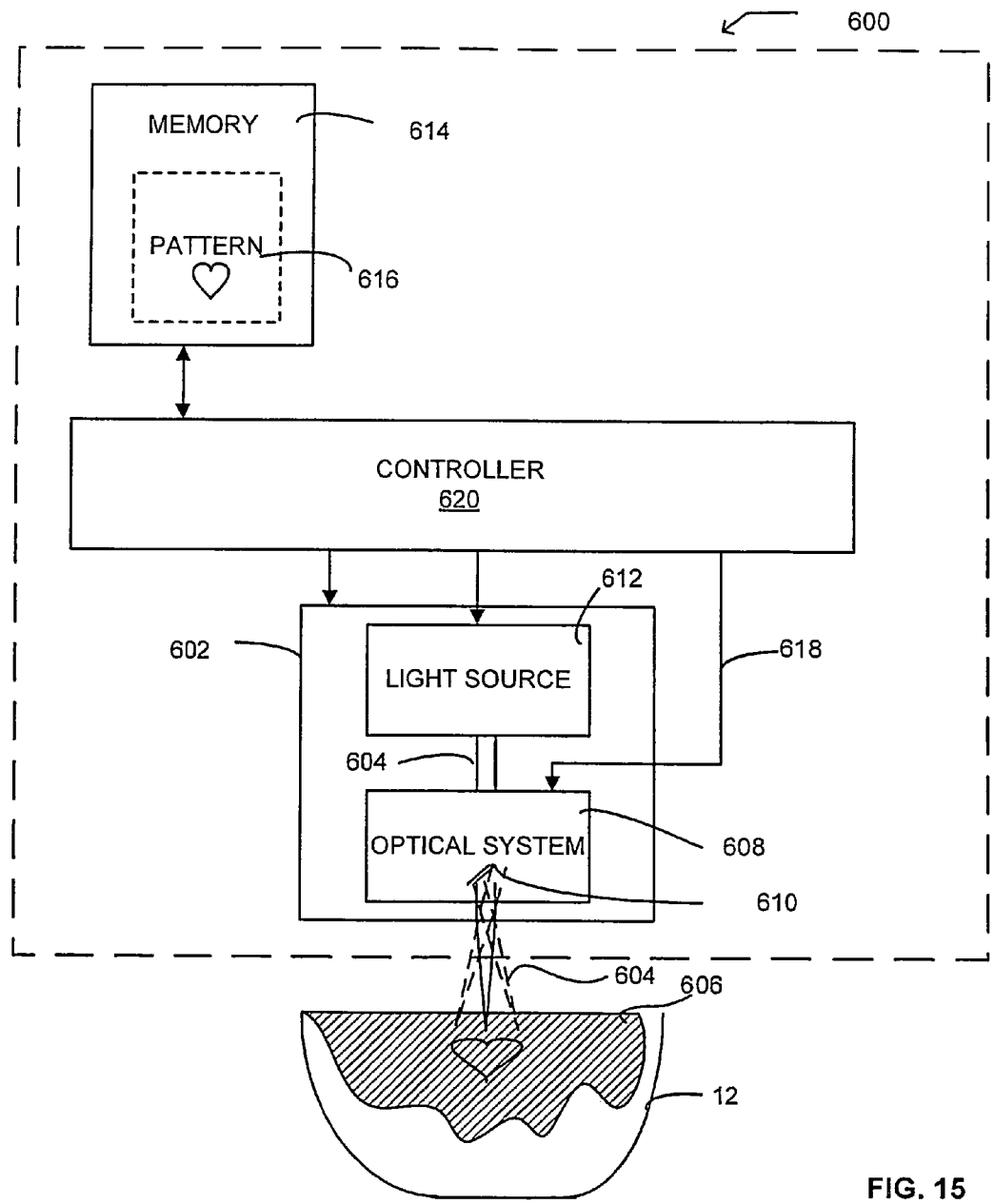
FIG. 15 is a block diagram of a system for targeted application of light to skin.

Patterned light may be delivered in the form of discrete pulses applied at multiple locations, as depicted in FIG. 14. Patterned light may also be delivered by sweeping a focused beam of light across a skin surface in a continuous pattern, for example, as depicted in FIG. 15. A beam may be moved across the skin surface with the use of a scanning mirror or functionally-equivalent optical systems of other types, the design and use of which is well known to those of skill in the art. Patterned light may also be delivered in some combination of continuous and discrete light; for example, a beam may be swept across the skin surface to form contiguous portions of a pattern, but turn on and off as the beam is moved to non-contiguous portions of the pattern.

FIG. 15 depicts a system 600 including a controllable positioning system 602 that may be used to move a beam of light 604 over a skin surface 606 and to adjust the positioning of light from the light source on a skin region. System 600 may include a controllable optical system 608 that includes one or more deflectors 610 configured to aim light 604, from the light source 612. The position of at least one deflector 610 may be controllable to aim light 604 toward at least one of the plurality of skin locations. Controllable optical system 608 may include a positioner adapted to adjust the position of light source 612. Light source 612 may be capable of producing light 604 of at least one defined wavelength band. System 600 may also include memory 614 capable of storing a pattern 616 in machine-readable form representing a plurality of locations within a skin region to which light 604 from light source 612 is to be directed. In some embodiments, system 600 may include one or more optical components capable of focusing light 604 from the light source 612 at a specific depth within a skin region 12 in response to a control signal 618, controller 620 configured to generate control signal 618 for driving controllable positioning system 602 to direct light onto a plurality of skin locations according to pattern 616 stored in memory 614. Controller 620 may be configured to generate a control signal from driving one or more optical components to adjust the focusing of light 604 at different depths and at different skin locations according to pattern 616. Deflectors 610 may be controllable deflectors configured to aim light 604 from light source 612, wherein the position of at least one of the one or more deflectors 610 is controllable to aim light toward any of the plurality of skin locations. Controller 620 may include one or more of hardware, software, and firmware. In some embodiments, controller 620 may include a microprocessor. In some embodiments, system 600 may include an imaging device, which may be for example, a CCD camera.

Figure 16:
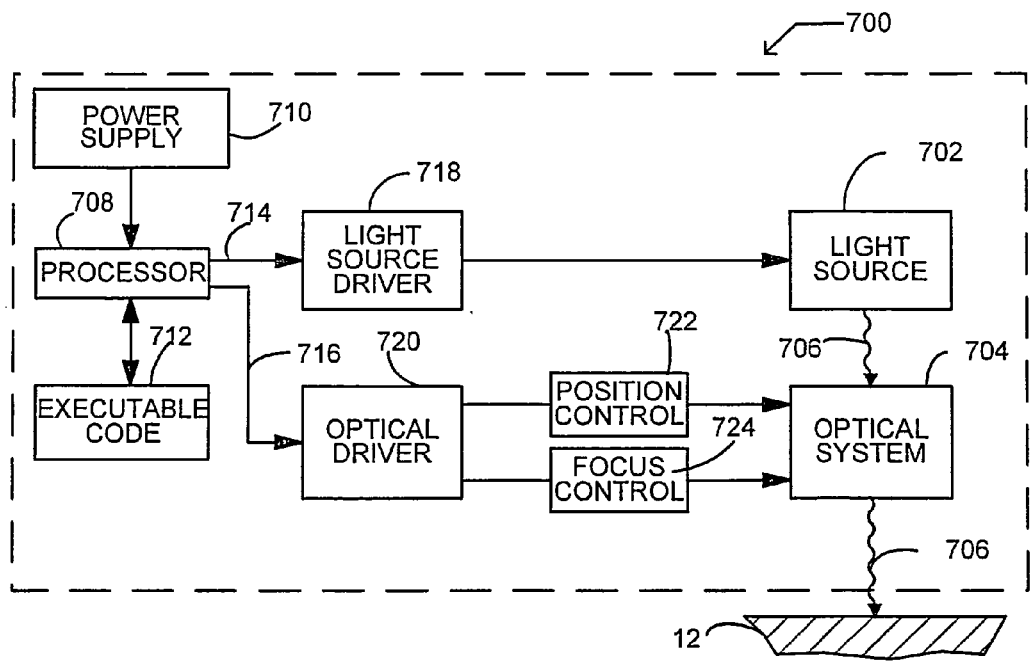
FIG. 16 is a block diagram of an embodiment of a system for controlled delivery of light to skin.

FIG. 16 is a block diagram of different aspects of a system 700 for delivering patterned light to a skin region 12. System 700 may include light source 702 and optical system 704, which directs and focuses light 706 from light source 702. Overall system operation may be controlled by processor 708, which may be, for example, a microprocessor, powered by power supply 710. Processor 708 may execute commands from executable code 712 to generate signals 714 and 716, which are sent to light source driver 718 and optical driver 720, respectively. Light source driver 718, which may include hardware, software, firmware, or a combination thereof, drives operation of light source 702. Optical driver 720, which also may include hardware, software, firmware, or a combination thereof, drives operation of optical system 704, via position control module 722 and focus control module 724. System 700 may be used to deliver targeted light to a plurality of locations under software control and/or under microprocessor control.

Figure 17:
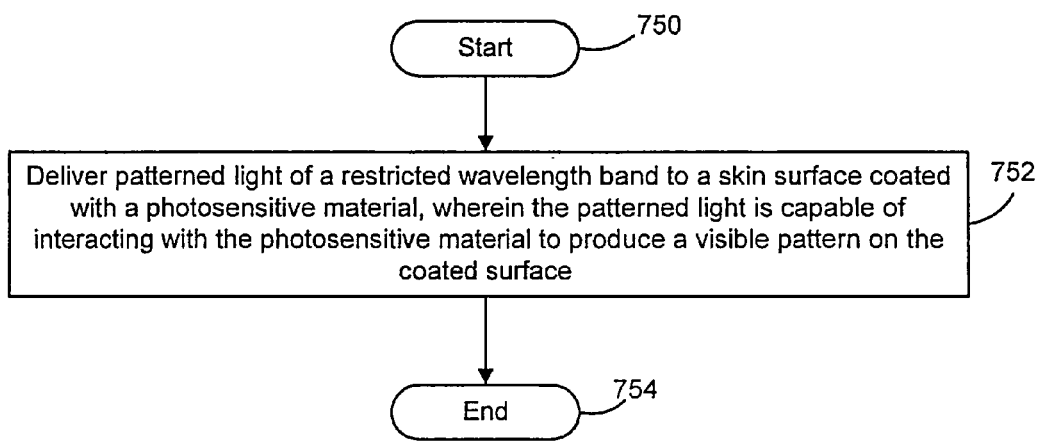
FIG. 17 is a flow diagram of a method producing a pattern on a surface.

FIG. 17 outlines a method that includes delivering patterned light of a restricted wavelength band to a skin surface coated with a photosensitive material, wherein the patterned light is capable of interacting with the photosensitive material to produce a visible pattern on the coated surface, as shown at step 752 of the flow diagram. The photosensitive material may be applied to the surface. Light may be delivered to different locations in sequence, in either discrete or continuous fashion. Patterned light as used in certain embodiments may be produced with the use of a controllable optical system that is controllable to focus the light source on at least two of a plurality of skin locations in sequence. In some embodiments, a controllable optical system may be used that is controllable to focus the light source on at least two of a plurality of skin locations simultaneously.

Figure 18A:
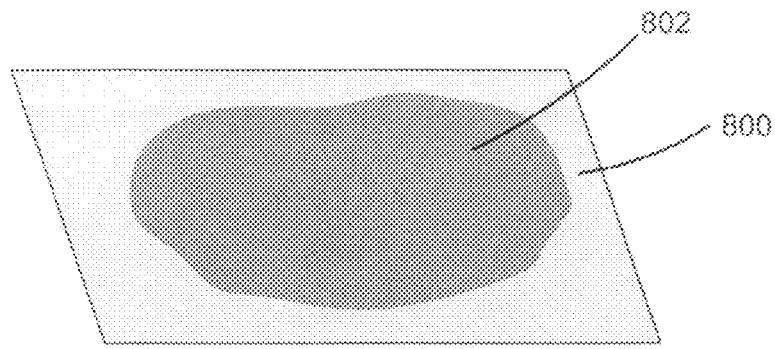
FIGS. 18A-18D depict steps of a method of patterning skin.
Figure 18B:
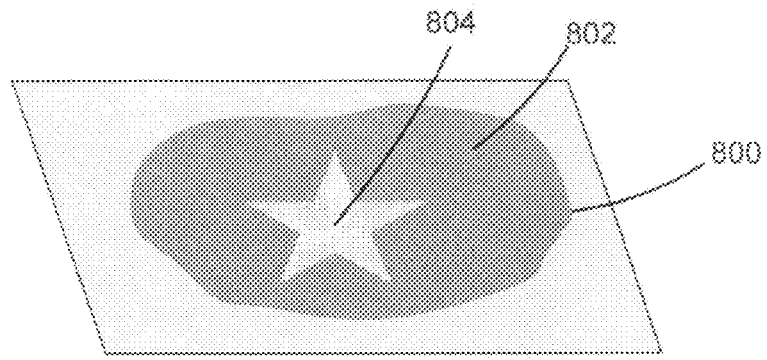
Figure 18C:
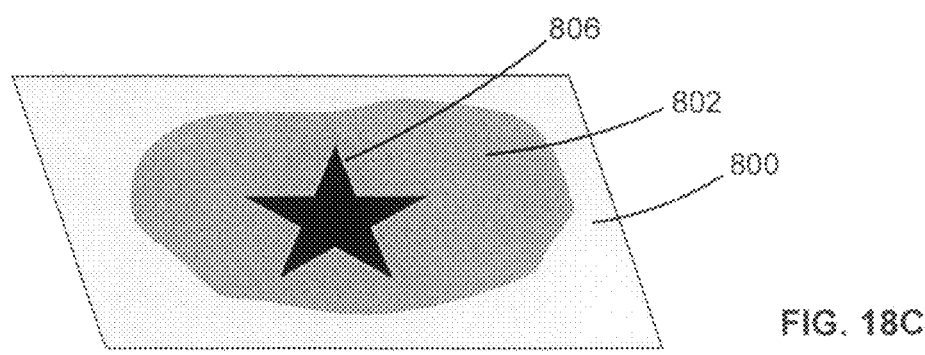
Figure 18D:
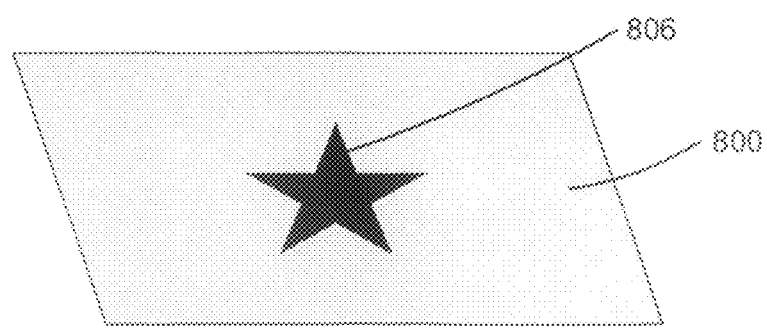

In some embodiments, light may be delivered to all parts of a pattern simultaneously. FIG. 18A illustrates a skin region 800 with a treated region 802 that contains a photoresponsive material. As described previously, photoresponsive material may be delivered to region 802 topically, by injection, or systemically. In step 18B, patterned light is delivered to area 804 in region 802 through the use of a stencil or mask or other methods as described herein below. Patterned light causes a reaction or transformation of photoresponsive material in area 804, to produce a pattern 806 of modified material as shown in FIG. 18C. In some embodiments, an additional step may be carried out to remove unmodified photoresponsive material from skin region 800, so that only pattern 806 remains in skin region 800, as depicted in FIG. 18D.

Figure 19A:
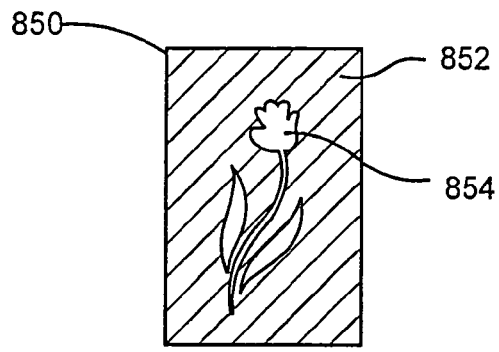
FIG. 19A illustrates an embodiment of a mask with a decorative pattern.
Figure 19B:
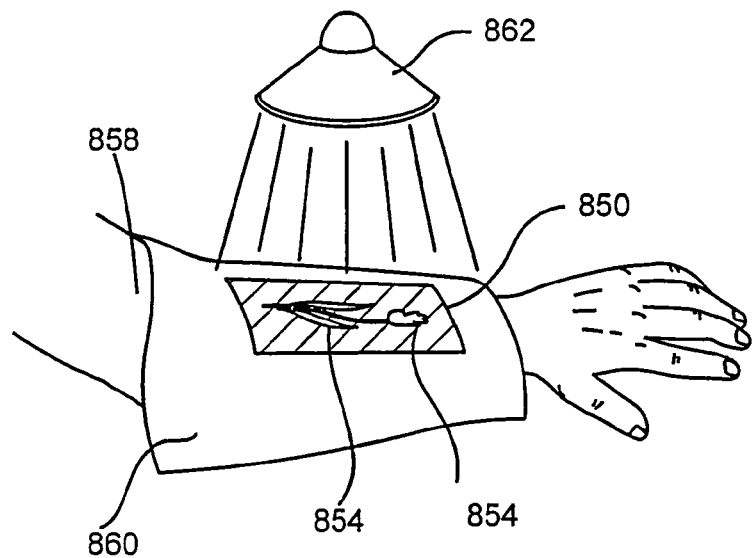
FIG. 19B depicts use of the mask depicted in FIG. 19A.
Figure 19C:
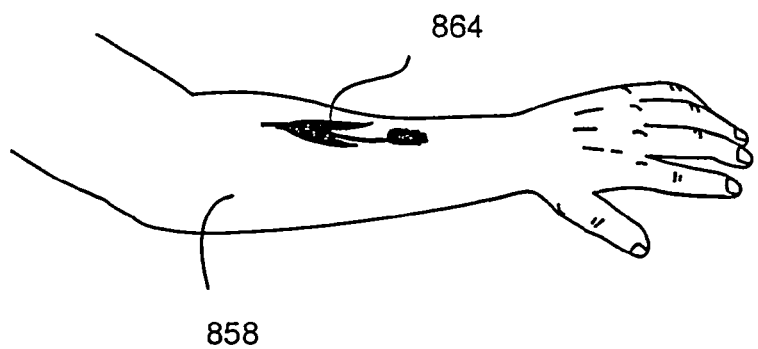
FIG. 19C illustrates a decorative pattern formed on a skin surface with the use of the mask depicted in FIG. 19A.

Several methods may be used to expose a treated skin region to patterned light. As shown in FIGS. 19A-19C, a mask (or stencil) 850 may be placed on the skin surface to block exposure of the skin surface to light except in the areas that are to be patterned. FIG. 19A depicts a mask 850 having an opaque portion 852 and a light transmitting portion 854. Mask 850 may be placed over a skin region that contains a photoresponsive material. In the example of FIG. 19B, the skin region is a portion of the arm 858 of a subject. A drape 860 may be used to extend the covered area of arm 858; various functionally equivalent configurations may be devised by a practitioner of skill in the relevant art. Light from light source 862 may cover all of the light transmitting portion 854 of mask 850, as depicted in FIG. 19B. In some alternative embodiments, light from a light source may cover a portion of a light transmitting portion of a mask, and the light source may be moved to one or more additional regions in order to expose all of the skin region exposed by the light transmitting portion of the mask. Light source 862 may be removed or turned off following exposure to light for a period of time sufficient to produce a desired modification of the photoresponsive material, and mask 830 and drape 860 (if used) removed. As shown in FIG. 19C, arm 858 of the subject, bears a patterned distribution 864 of modified photoresponsive material that corresponds to the light transmitting regions 854 of mask 850.

Figure 20:
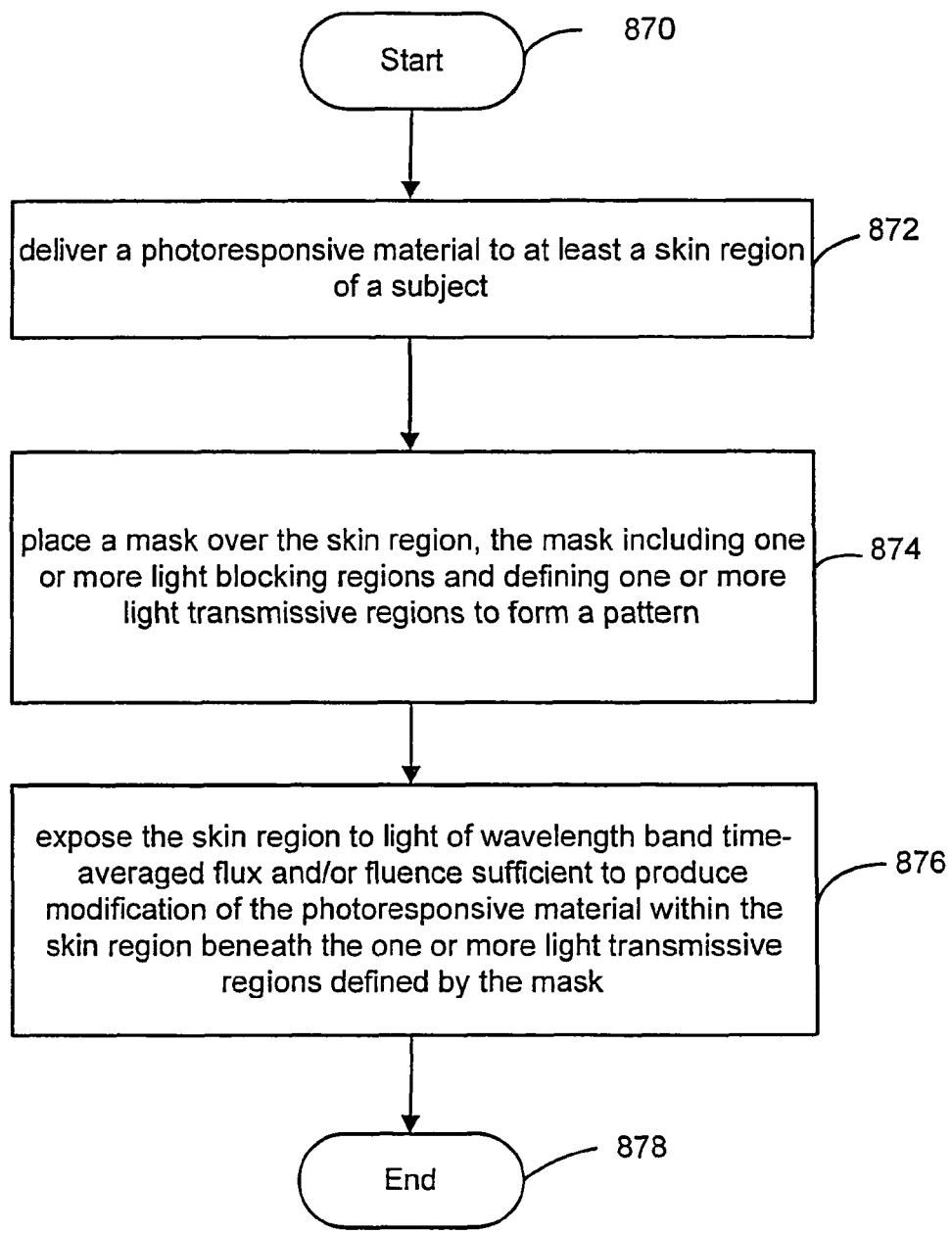
FIG. 20 is a flow diagram of a method of forming a patterned distribution of material in skin.

The method illustrated in FIGS. 19A-19C is summarized in FIG. 20. At step 872, a photoresponsive material is delivered to at least a skin region of a subject. At step 874, a mask is placed over the skin region, the mask including one or more light blocking regions and defining one or more light transmissive regions to form a pattern. At step 876, the skin region is exposed to light of wavelength band, time-averaged flux and/or fluence sufficient to produce modification of the photoresponsive material within the skin region beneath the one or more light transmissive regions defined by the mask. Delivering a photoresponsive material may include delivering a photoresponsive material that is converted from an active form to an inactive form by exposure to light. Alternatively, delivering a photoresponsive material may include delivering a photoresponsive material that is converted from an inactive form to an active form by exposure to light. In further embodiments, the method may also include reversing the photo reaction by exposing the skin region to light of a wavelength band, time-averaged flux and/or fluence sufficient to reverse the reaction. Photo reactions that may operate in a first direction at a first wavelength band, time-averaged flux and/or fluence, and which may be reversed at a second wavelength band, time-averaged flux and/or fluence include, for example crosslinking of PEG-cinnamylidine acetate as described in U.S. Pat. No. 5,990,193, and reactions of various aromatic diazo dyes, as described in U.S. Pat. No. 5,998,588, both of which are incorporated herein by reference in their entirety.

Figure 21A:
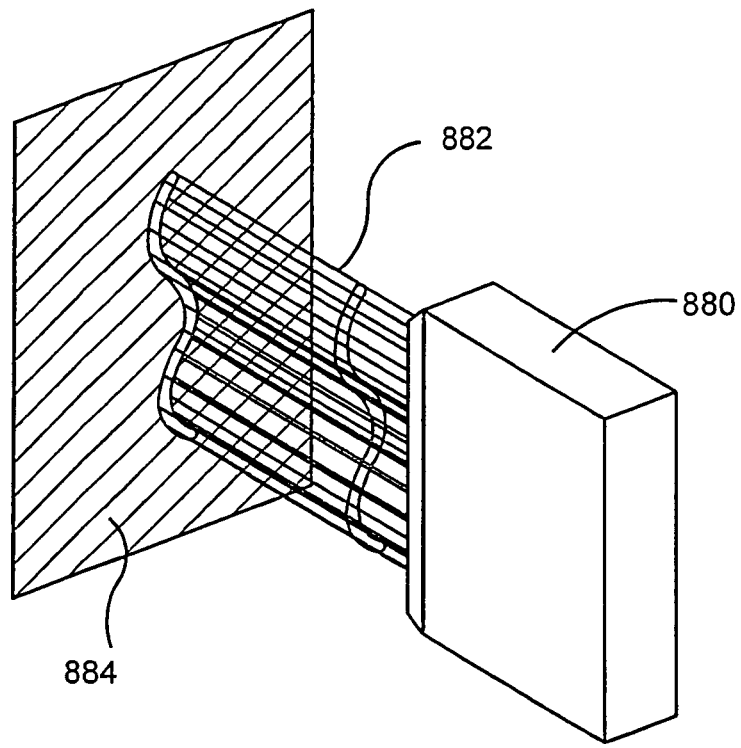
FIG. 21A illustrates delivery of patterned light to a treated skin surface.
Figure 21B:
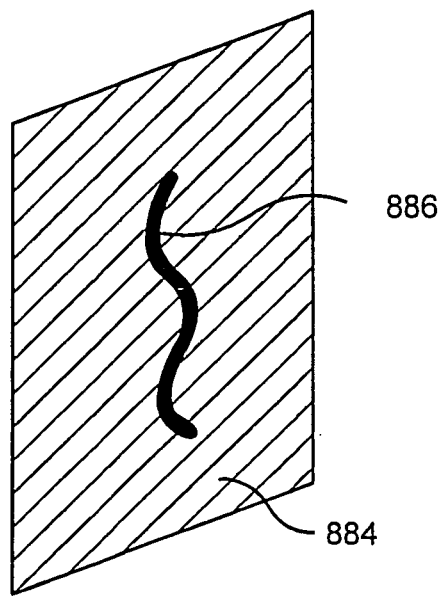
FIG. 21B illustrates a pattern formed on a skin surface by the patterned light depicted in FIG. 21A.

An alternative method of delivering patterned light is depicted in FIGS. 21A and 21B. FIG. 21A depicts a light source 880 that produces patterned light 882. This may be accomplished by placing a mask over a single light source of sufficient size and capable of generating substantially collimated light, or by placing multiple smaller light sources, also capable of producing relatively parallel light, in a suitable arrangement. Patterned light 882 from light source 880 may then be delivered to a treated surface 884. In the example of FIG. 21A, treated surface 884 need not be masked, because the light is patterned, although in some embodiments patterned light may be used in combination with a mask or stencil. FIG. 21B illustrates pattern 886 that has been formed by modification of photoresponsive material in or on treated surface 884 by exposure to patterned light 882.

Figure 22:
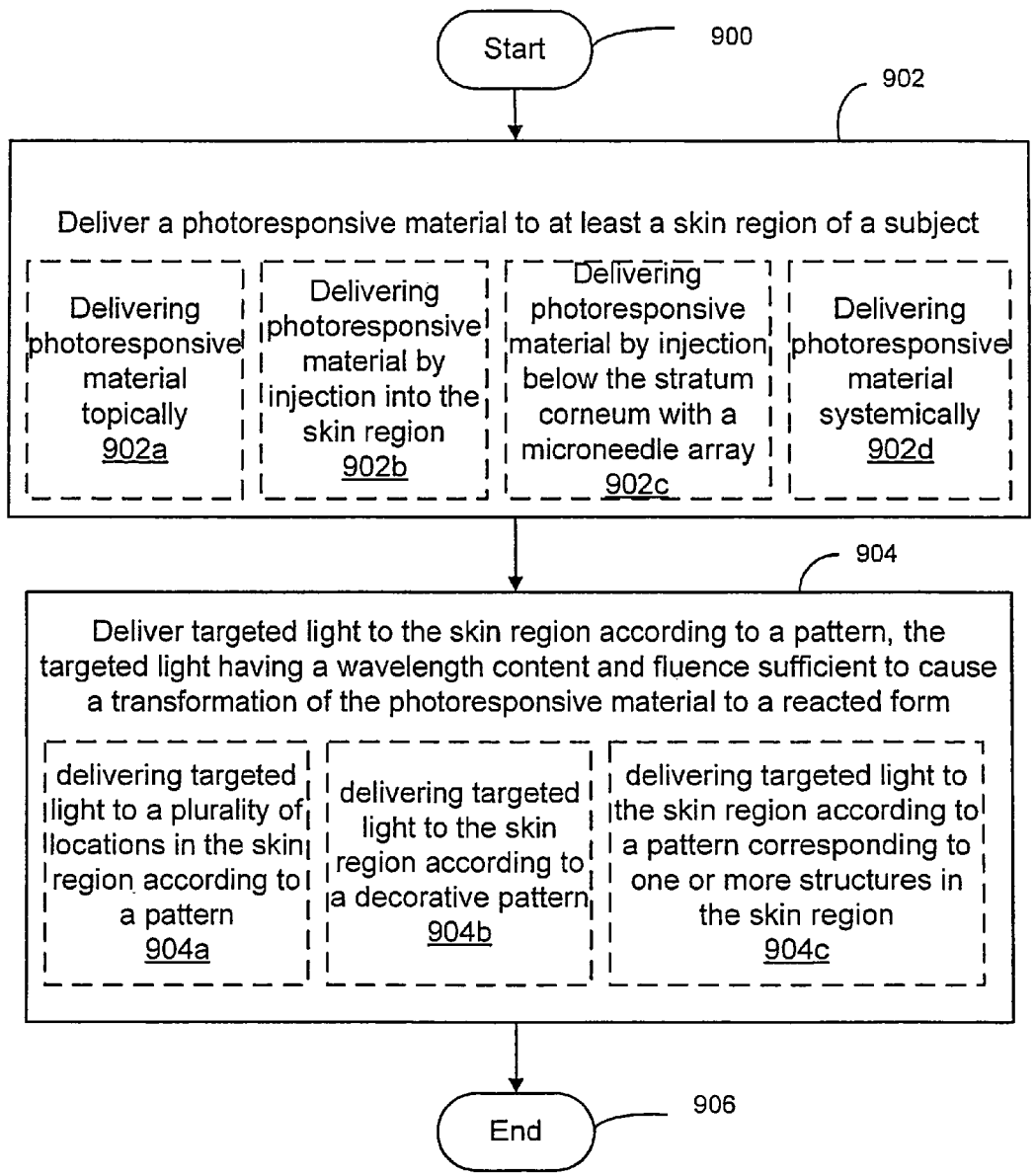
FIG. 22 is a flow diagram illustrating variations of methods for photopatterning of skin.

As illustrated in FIG. 22, various methods of delivering photoresponsive material to a skin region may be combined with various methods of delivering targeted light to a skin region to produce a number of related embodiments. Delivering photoresponsive material to at least a skin region, at step 902, may be further characterized as delivering photoresponsive material topically (step 902a), delivering photoresponsive material by injection in the skin region (902b) by delivering photoresponsive material by injection below the stratum corneum with a microneedle array (902c), or delivering the photoresponsive material systemically (902d). Delivering targeted light to the skin region according to a pattern, as at step 904, may be performed by a number of approaches, including delivering targeted light to a plurality of locations in the skin region according to a pattern (904a), delivering targeted light to the skin region according to a decorative pattern (step 904b) or delivering targeted light to the skin region according to a pattern corresponding to one or more structures in the skin region (step 904c). Methods including step 904c may also include a step of detecting one or more features in the skin region. The target light may have a wavelength content, time-averaged flux, or fluence sufficient to cause a transformation of the photoresponsive material to a modified form.

Figure 23A:
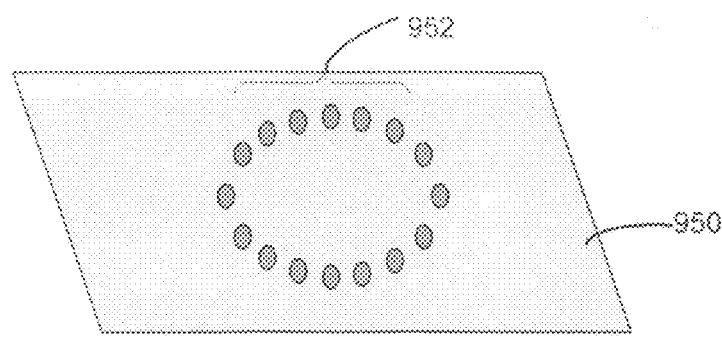
Figure 23B:
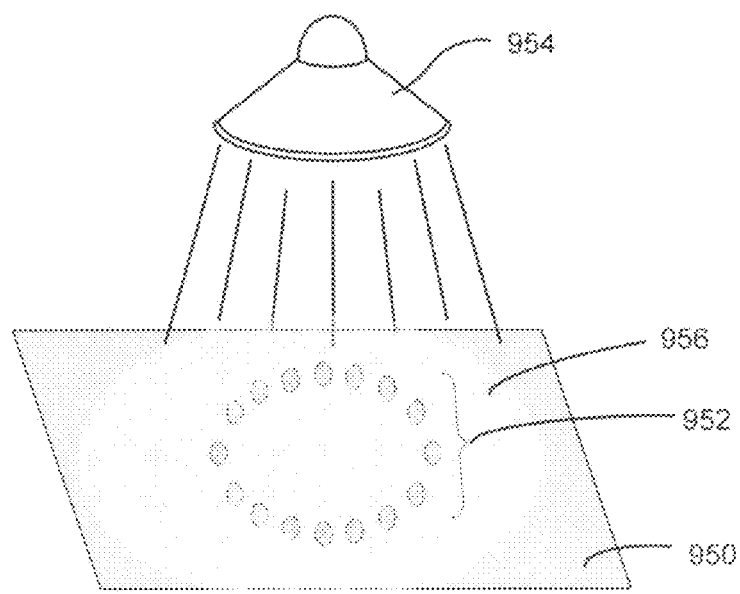
Figure 23C:
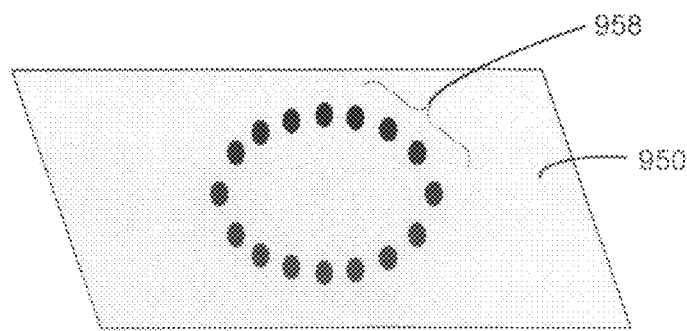
Figure 24:
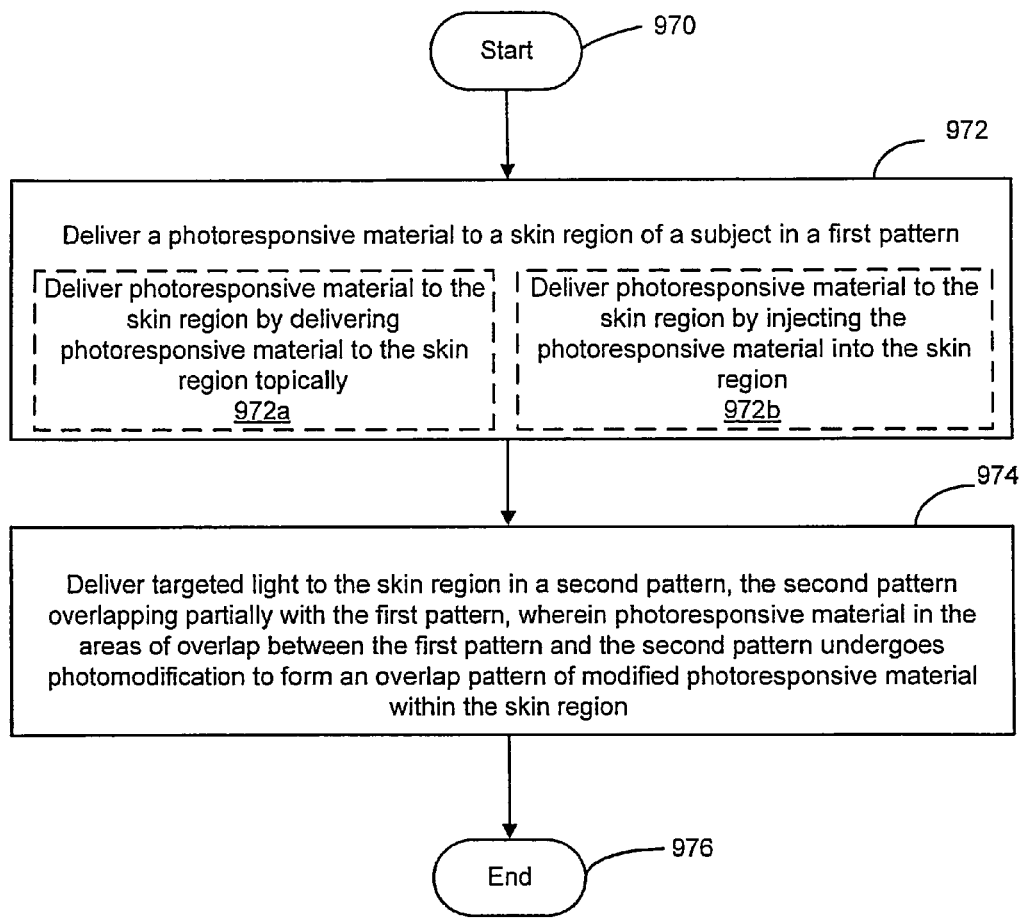
FIG. 24 is a flow diagram illustrating variations of methods for photopatterning of skin.

In some embodiments, a photoresponsive material may be introduced into a skin region in a patterned distribution, and light delivered to the skin in a relatively non-targeted fashion in order to cause transformation of the photoresponsive material to a modified form. This approach is illustrated in FIGS. 23A-23C. A photoresponsive material may be delivered topically in a pattern by various methods, including painting, printing (i.e., ink-jet or wire-jet printing), and stenciling, for example. Photoresponsive material may be delivered into the skin, below the skin surface, by injection with one or multiple needles (e.g. tattoo needles, micro-needle array, hypodermic needle) or by a pressure jet.

FIG. 23A illustrates a skin region 950 including a patterned distribution of photoresponsive material 952. In FIG. 23B, light source 954 is used to deliver light to a region 956 which includes patterned distribution of photoresponsive material 952. Light source 954 delivers light in a relatively non-targeted fashion; any light distribution that covers patterned distribution of photoresponsive material 952 with light of sufficient intensity or fluence may be used. In some embodiments, light may be delivered in several stages or from several sources, e.g., by delivering light from two or more sources, or from the same source at two different times, such that each individual delivery of light covers only a part of the patterned distribution of photoresponsive material, but that together, the multiple deliveries of light cover the entire patterned distribution of photoresponsive material. In FIG. 23C, following modification of photoresponsive material due to light exposure, a patterned distribution of modified material 958 is present in skin region 950.

Figure 25A:
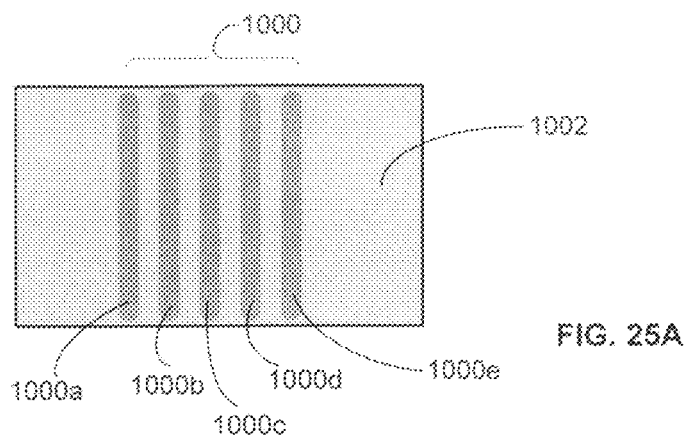
FIGS. 25A-25C illustrate patterning of skin by patterned delivery of photoresponsive material combined with patterned delivery of light.
Figure 25B:
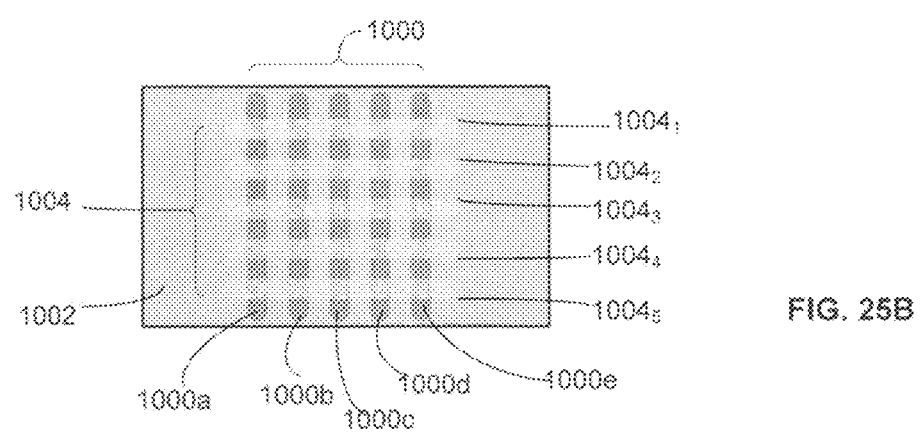
Figure 25C:
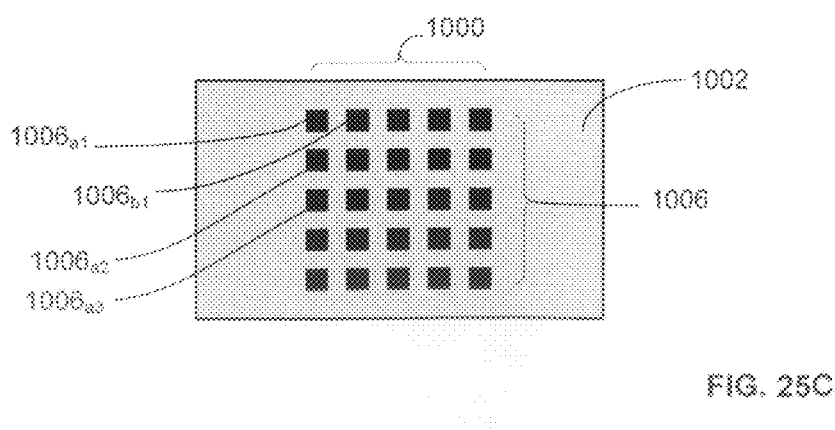

In some embodiments, both photoresponsive material and light may be delivered to the skin in a pattern. Patterned delivery of photoresponsive material and of light may be accomplished by any of the exemplary methods described herein above, for example. The patterns may be substantially similar and overlapping, in which case the distribution pattern of the modified form in or on the skin will be substantially the same as the distribution patterns of the unmodified form and the light. If the distribution pattern of the photoresponsive material and the distribution pattern of the light are partially overlapping, a patterned distribution of the modified form may be obtained that is defined by the shape and distribution of the regions of overlap between the distribution patterns of photoreactive material and light. This approach is illustrated in FIG. 24 and FIGS. 25A-25C. At step 972 of FIG. 24, a photoresponsive material is delivered to a skin region of a subject in a first pattern. In one exemplary variant, 972a, photoresponsive material is delivered to the skin region topically. In another exemplary variant 972b, photoresponsive material 972b is delivered to the skin region by injection (e.g., via a hypodermic needle, tattoo needle, microneedle array, pressure jet, etc.) At step 974, targeted light is delivered to the skin region in a second pattern, the second pattern overlapping partially with the first pattern. The photoresponsive material in the areas of overlap between the first pattern and the second pattern may undergo photomodification to form an overlap pattern of modified photoresponsive material within the skin region. The method is illustrated in graphic form in FIGS. 25A-25C. In FIG. 25A, a patterned distribution of photoresponsive material 1000 is formed in skin region 1002. In the present example, patterned distribution of photoresponsive material 1000 includes five lines of photoresponsive material $1000_a$, $1000_b$, $1000_c$, $1000_d$, and $1000_e$. Such a patterned distribution may be formed by printing, injection, or other methods as described herein or as may be devised by one of skill in the art. In FIG. 25B, a patterned distribution of light 1004 is delivered to skin region 1002, overlapping patterned distribution of photoresponsive material 1000. Patterned distribution of light 1004 in this example includes five lines of light, $1004_1$, $1004_2$, $1004_3$, $1004_4$, and $1004_5$, which may be formed by various methods as described previously. Following exposure to light, the photoresponsive material may react to form the patterned distribution 1006 of modified material in skin region 1002, as shown in FIG. 25C. Patterned distribution 1006 includes regions $1006_{rc}$, where r=1 . . . 5 and c=a . . . e, formed by areas of overlap between patterned distribution of photoresponsive material 1000 and patterned distribution of light 1004.

Figure 26:
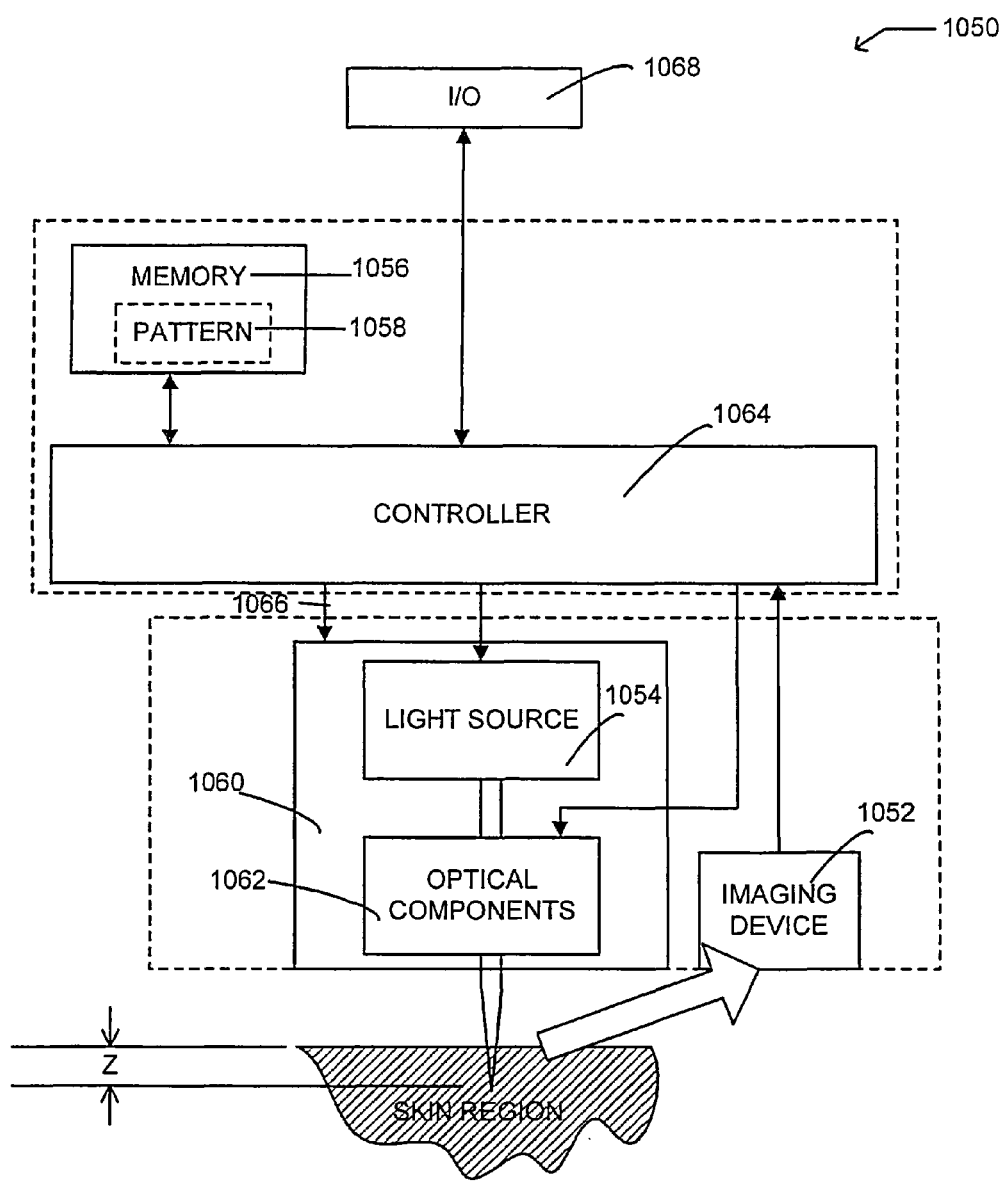
FIG. 26 is a block diagram of a system for photopatterning of skin.

In some embodiments, it may be desirable to detect an image of a skin region in which a patterned distribution of a material is to be formed. For example, it may be desirable to detect a feature in a skin region that may be a treatment target, prior to delivery of a treatment in a targeted or aligned fashion. Or, it may be desirable to view an image of the skin region in order to determine placement of a decorative pattern in or on the skin region, e.g, aligned relative to a portion of a previously-emplaced pattern. FIG. 26 is a block diagram of a system 1050 that includes an imaging device 1052. System 1050 may include a light source 1054 capable of producing light of at least one defined wavelength band, memory 1056 capable of storing a pattern in machine-readable form representing a plurality of locations within a skin region to which light from the light source is to be directed, controllable positioning system 1060 configured to adjust the positioning of light from light source 1054 on a skin region, one or more optical components 1062 capable of focusing light from the light source 1054 at a specific depth within a skin region in response to a control signal, and controller 1064 configured to generate a control signal 1066 for driving controllable positioning system 1060 to direct light onto a plurality of skin locations according to the pattern 1058 stored in memory 1056. In some embodiments, controller 1064 may be configured to generate control signal 1066 for driving optical components 1062 to adjust the focusing of light at different depths and at different skin locations according to pattern 1058 stored in memory 1056. In some embodiments, controllable positioning system 1060 includes one or more controllable deflectors configured to aim light from light source 1054, wherein the position of at least one of the deflectors is controllable to aim light toward any of the plurality of skin locations. System 1050 may also include one or more I/O devices 1068 to provide for entry of control inputs by a user and for the presentation of information or data to the user. Various types of I/O devices are known or may be developed by those of skill in the arts of electronics and sensors for receipt and presentation of information and data in audio, visual, electronic, tactile, or other form, examples of which include scanners, touchscreens, keyboards, mice, trackballs, buttons, dials, microphones, speakers, video displays, etc. Controller 1064 may include one or more of hardware, software, and firmware. In some embodiments, controller 1064 may include a microprocessor. System 1050 may include an imaging device, which may be, for example, a CCD camera.

In various embodiments, examples of which are described herein, photoresponsive materials may be delivered to at least a skin region of a subject, and some or all of the photoresponsive material may be exposed to light to cause a reaction or conversion of the photoresponsive material. In some applications it may be desirable to remove one or both of modified and unmodified material from the subject's body. Unwanted material may be removed by processes normally occurring in the body, such as metabolism or excretion of the material, or by sluffing of skin containing the material. In some cases, materials may not be removed by naturally occurring processes, or may not be removed as quickly as is deemed desirable, and further treatment steps may be used to remove the materials form the body. In some embodiments, unmodified material may be removed, while modified material may be left in the skin region. In some embodiments, modified material may be removed from the skin region after a use period. Treatment to removed either modified or unmodified photoresponsive material, or both, may include phototreatment (e.g., photobleaching), chemical treatment (e.g., chemical bleaching), chemo-mechanical treatment, or treatment by exposure to heat, vibration, electromagnetic fields, among others.

Figure 27:
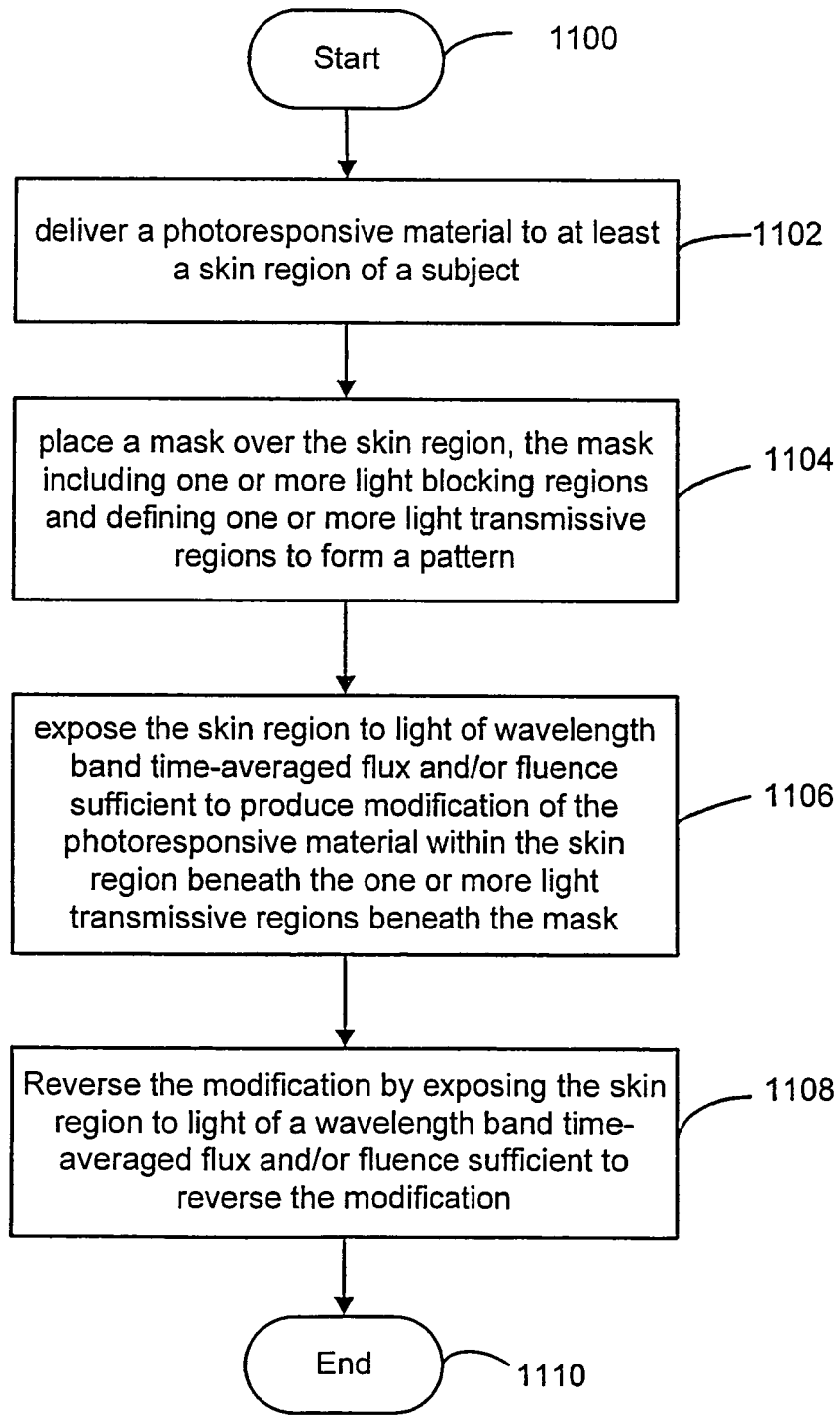
FIG. 27 is a flow diagram of a method of photopatterning skin including reversing the photoreaction.

FIG. 27 depicts an exemplary sequence of method steps. At step 1102, a photoresponsive material is delivered to at least a skin region of a subject. At step 1104, a mask is placed over the skin region, the mask including one or more light blocking regions and defining one or more light transmissive regions to form a pattern. At step 1106, the skin region may be exposed to light of wavelength band, time-averaged flux and/or fluence sufficient to produce modification of the photoresponsive material within the skin region beneath the one or more light transmissive regions beneath the mask. Method steps 1102 through 1106 correspond to the method illustrated in FIGS. 19A-19C, for example. At step 1108, the modification is reversed by exposing the skin region to light of wavelength, time-averaged flux and/or fluence sufficient to reverse the modification.

Various of the methods disclosed herein (for example, the method as outlined in FIG. 12), may include removal of the modified form of the photoresponsive material from the skin region over time. In some embodiments, the modified form may be removed from the skin region by metabolism. The modified form may be removed from the skin region through sluffing of dead skin cells and/or the continual shedding of epidermal outer layers, for example. In some embodiments, the modified form may be removed from the skin region after a treatment period. The method may include removing the modified form by a photo treatment, by a chemical treatment, or by a chemo-mechanical treatment.

Figure 28:
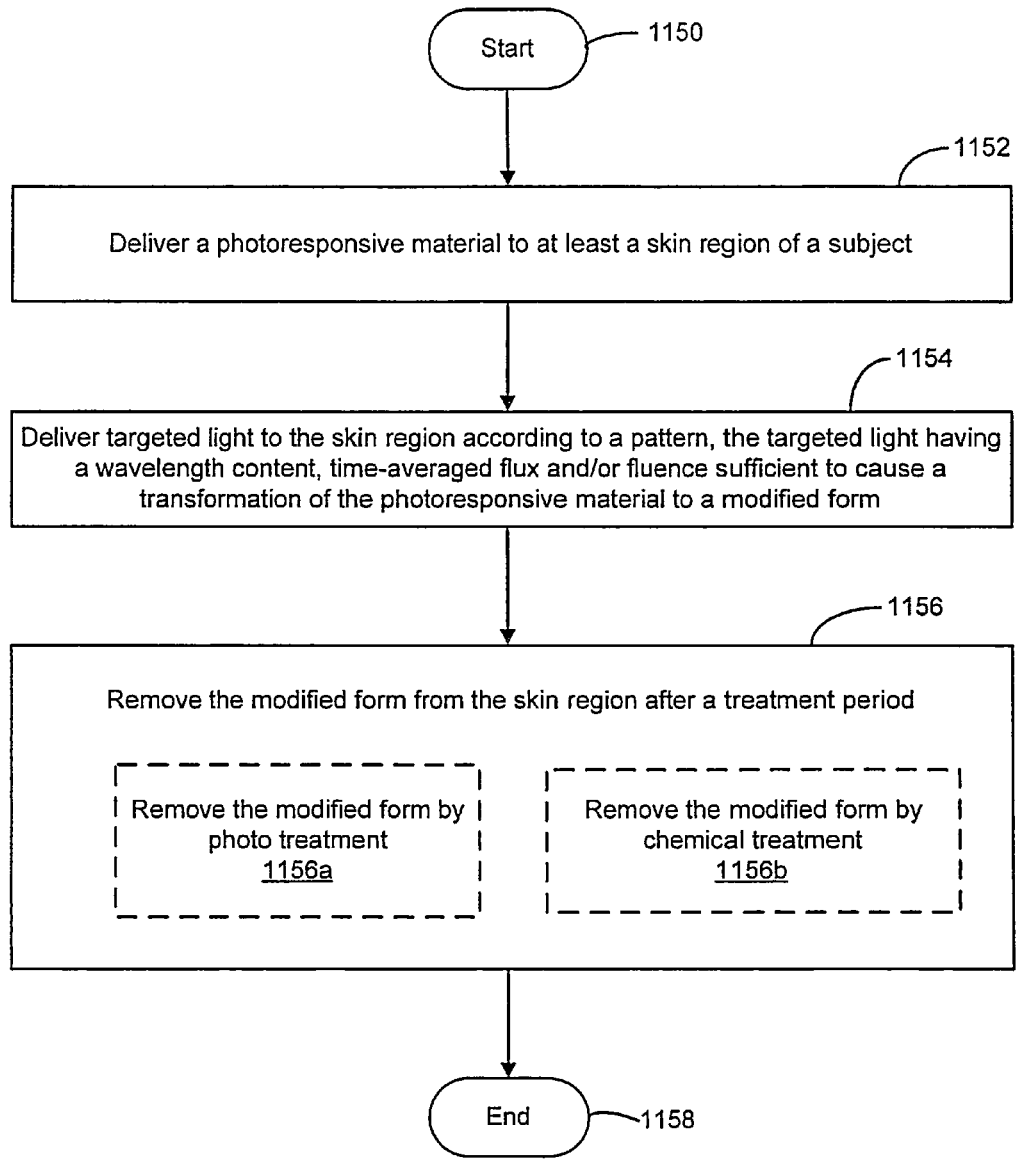
FIG. 28 is a flow diagram of a method of photopatterning skin including removing the modified form of the photoresponsive material.

FIG. 28 depicts steps of a method that includes removing the modified form of the photoresponsive material from the skin region after a treatment period. At step 1152, a photoresponsive material is delivered to at least a skin region of a subject. At step 1154, targeted light is delivered to the skin region according to a pattern, the targeted light having a wavelength content, time-averaged flux and/or fluence sufficient to cause a transformation of the photoresponsive material to a modified form. At step 1156, the modified form is removed from the skin region after a treatment period. The modified form may be removed by photo treatment (step 1156a) or by chemical treatement (1156b), for example. The treatment period may be quite brief, producing only a transient presence of the modified material in the system, or may be of extended duration, of hours, days, weeks, months, or even years.

Examples of photoresponsive materials that may be used in various embodiments include, but are not limited to photodynamic therapy agents, photochromic dyes and pigments, photo-crosslinkable materials, photopolymerizable materials, and photodimerizable materials, luminides, light reactive polymers that change in conformation, volume, binding activity, drug activity, hydrogels of various types. Various exemplary photoresponsive materials are described in U.S. Pat. Nos. 6,602,975; 5,998,588; 6,555,663; 5,990,193; and 6,818,018, which are incorporated herein by reference in their entirety. Photoresponsive materials may be cosmetic materials having selected color or other appearance properties. Reaction undergone by photoresponsive materials may be a reversible transformation or an irreversible transformation. In some embodiments, the transformation may convert the photoresponsive material from an active to an inactive form. In other embodiments, the transformation may convert the photoresponsive material from an inactive to an active form. The transformation may include, for example, conversion of a photoresponsive material from a substantially colorless form to a colored form, or from a colored form to a substantially colorless form. Examples of photochromic dyes are listed in U.S. Pat. No. 6,602,975, which is incorporated herein by reference. In some embodiments, the transformation may include conversion of the photoresponsive material from a first color to a second color, or may modify the extent to which it scatters light of a given waveband. The modified form may be visible under natural light in some embodiments. In some embodiments, the modified form may be visible under ultraviolet light. In some embodiments, the modified form may be fluorescent. The modified form may be a pigment, dye, pharmaceutical compound, or cosmetic material.

Figure 29:
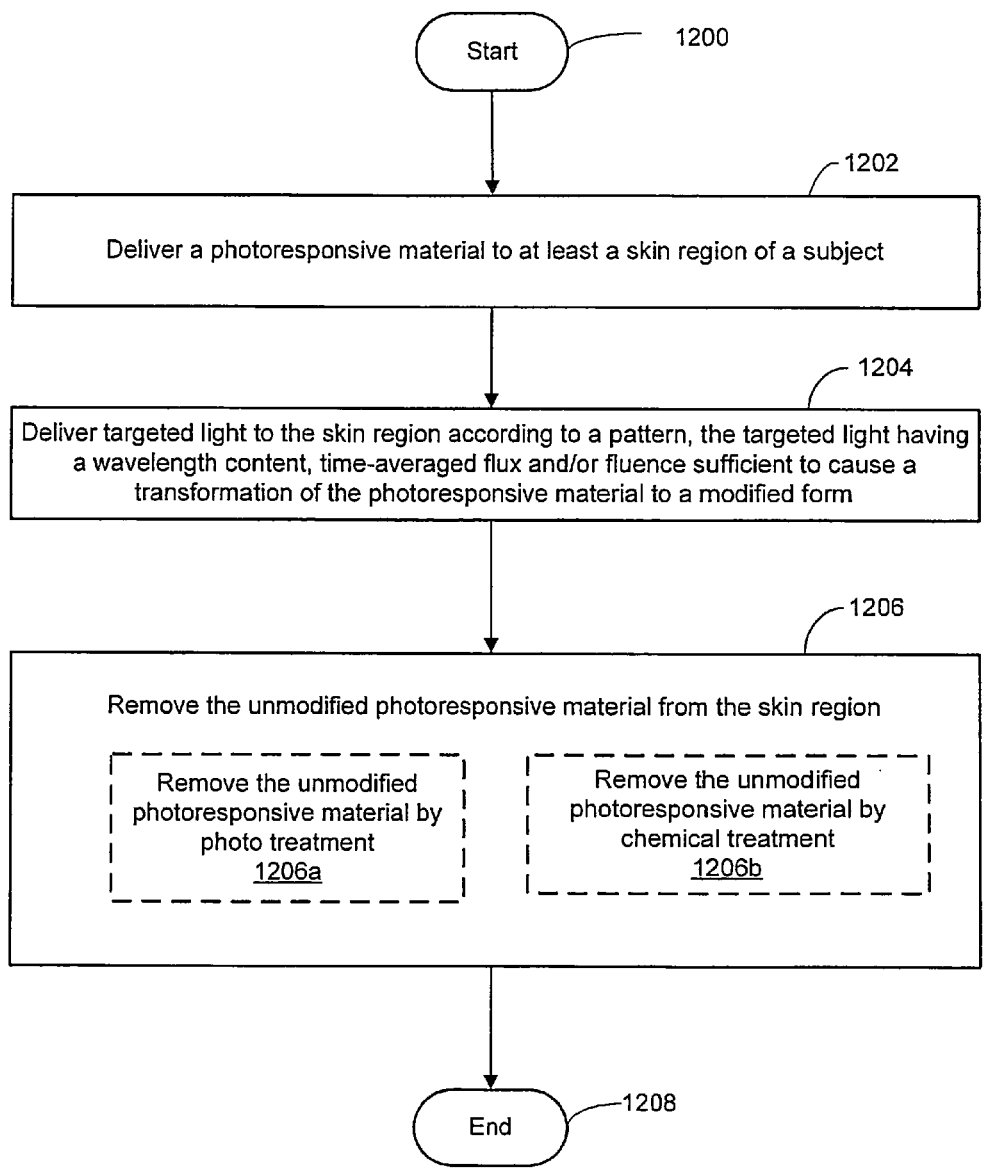
FIG. 29 is a flow diagram of a method of photopatterning skin including removing unmodified photoresponsive material from the skin.

FIG. 29 depicts steps of a method that includes removing unmodified photoresponsive material from a skin region of a subject. At step 1202, a photoresponsive material is delivered to at least a skin region of a subject. At step 1204, targeted light is delivered to the skin region according to a pattern, the targeted light having a wavelength content, time-averaged flux and/or fluence sufficient to cause a transformation of the photoresponsive material to a modified form. At step 1206, the unmodified photoresponsive material is removed from the skin region. The unmodified photoresponsive material may be removed by phototreatment, as shown in step 1206a, or by chemical treatment, as shown in step 1206b.

Figure 30:
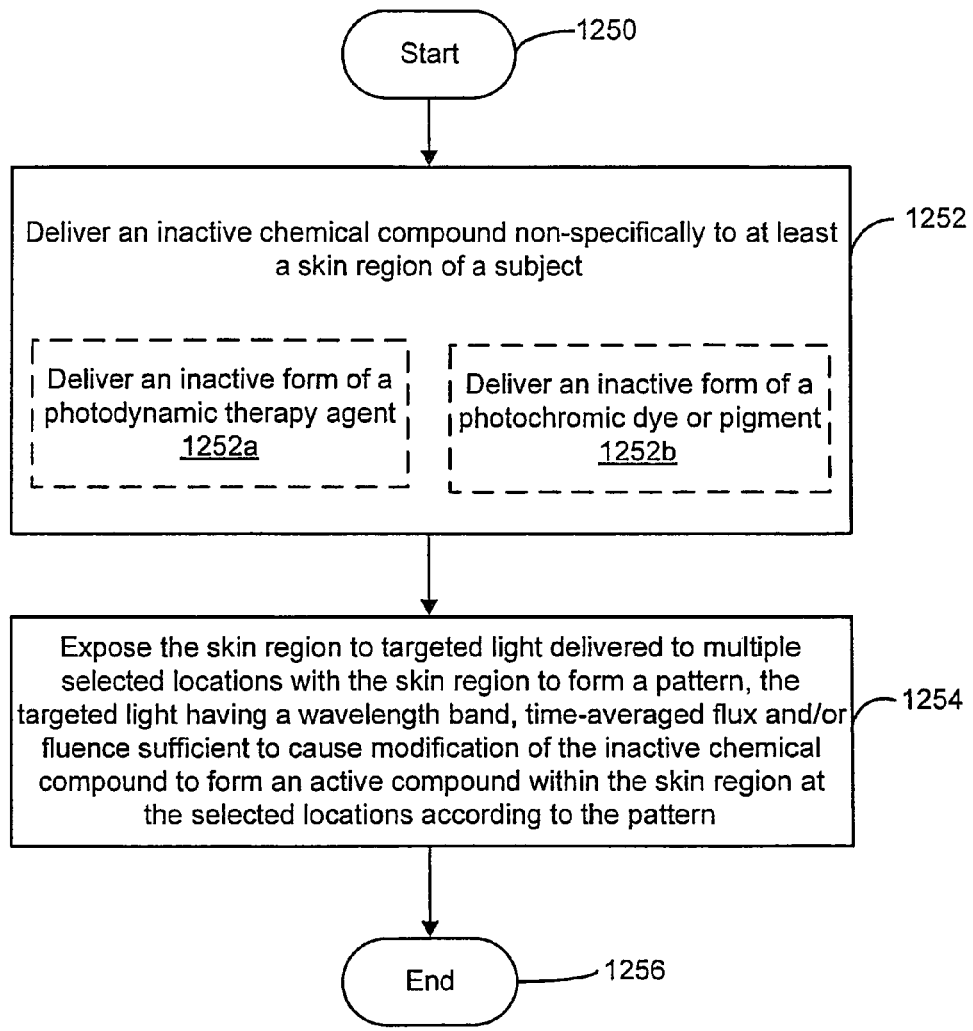
FIG. 30 is a flow diagram of a method of photopatterning an active chemical compound in the skin.

FIG. 30 illustrates a method of providing controlled delivery of an active compound to a skin region, which includes delivering an inactive chemical compound non-specifically to at least a skin region of a subject at step 1252 and exposing the skin region to targeted light delivered to multiple selected locations within the skin region to form a pattern at step 1254, the targeted light having a wavelength band, time-averaged flux and/or fluence sufficient to cause modification of the inactive chemical compound to form an active compound within the skin region at the selected locations according to the pattern. As illustrated by steps 1252a and 1252b, respectively, delivering an inactive chemical compound may include delivering an inactive form of a photodynamic therapy agent or a photochromic dye or pigment. It is within the present inventive scope to deliver two-or-more materials in this manner, and to induce reactions between the two-or-more of them or between the two-or-more of them and ambient materials by the action of the incident light.

Systems for the delivery of light to skin, as described herein, may include various types of light sources. In general, light sources must deliver light having wavelength content, fluxes and fluences sufficient to produce a particular effect in the photoresponsive material that is being exposed to the light. For example, in some embodiments, the light may have a wavelength content, time-averaged flux and/or fluence sufficient to cause a photo cross-linking reaction of the photoresponsive material. In other embodiments, the light may have wavelength content, time-averaged flux and/or fluence sufficient to cause a photochromic reaction of the photoresponsive material. In still other embodiments, the light may have a wavelength content, time-averaged flux and/or fluence sufficient to cause a photodimerization reaction of the photoresponsive material. Light sources suitable for use in various embodiments as described herein include lasers, laser diodes, as well as various non-coherent light sources. Light sources may include light emitting diodes. In some embodiments, light sources may emit light in an ultraviolet wavelength band. In some embodiments, light sources may emit light in a visible wavelength band, or in an infrared one. Broad-band light sources may be used in some embodiments.

Figure 31:
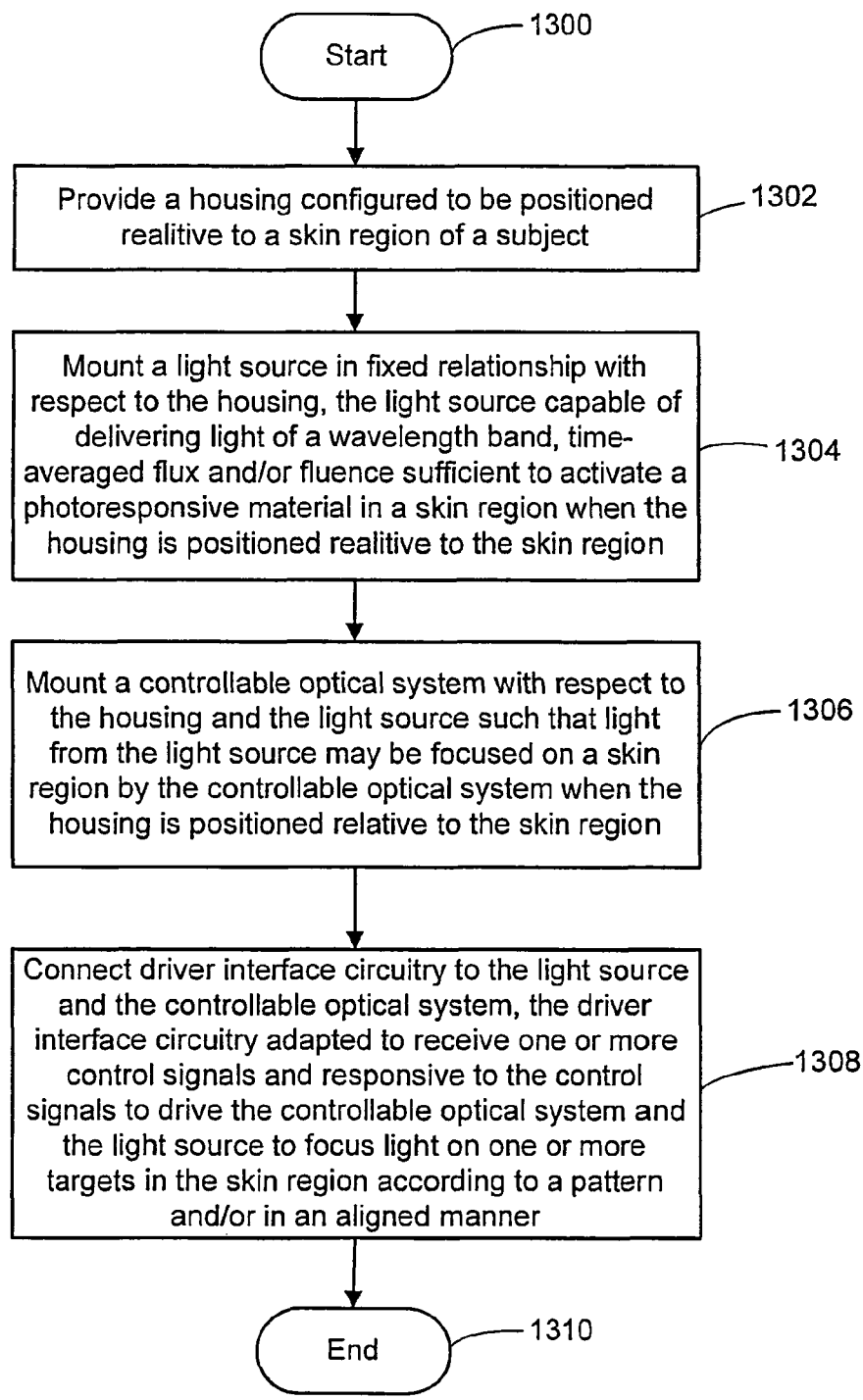
FIG. 31 is a flow diagram of a method of manufacturing a device for delivering patterned light.

FIG. 31 depicts a method of manufacturing a targeted light delivery system. Step 1302 includes providing a housing configured to be positioned relative to a skin region of a subject. At step 1304, a light source is mounted in fixed relationship with respect to the housing, the light source capable of delivering light of a wavelength band, time-averaged flux and/or fluence sufficient to activate a photoresponsive material in a skin region when the housing is positioned realitive to the skin region. At step 1306, a controllable optical system is mounted with respect to the housing and the light source such that light from the light source may be focused on a skin region by the controllable optical system when the housing is positioned relative to the skin region. At step 1308, driver interface circuitry is connected to the light source and the controllable optical system, the driver interface circuitry adapted to receive one or more control signals and responsive to the control signals to drive the controllable optical system and the light source to focus light on one or more targets in the skin region according to a pattern and/or in an aligned manner.

Figure 32:
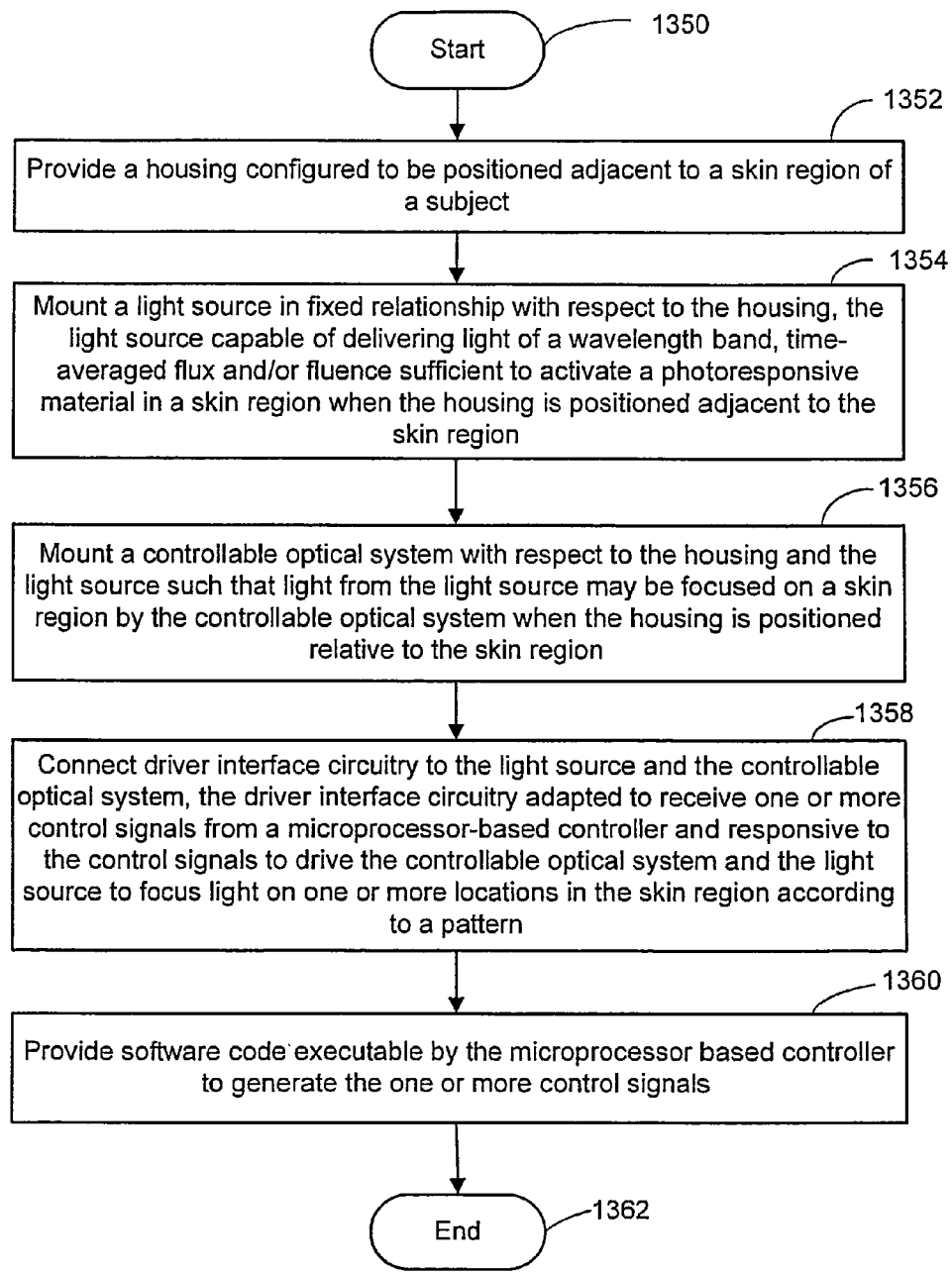
FIG. 32 is a flow diagram of a further method of manufacturing a device for delivering patterned light.

FIG. 32 depicts a method of manufacturing a device for delivering patterned light. A housing is provided that is configured to be positioned adjacent to a skin region of a subject. At step 1354, a light source is mounted in fixed relationship with respect to the housing, the light source capable of delivering light of a wavelength band, time-averaged flux and/or fluence sufficient to activate a photoresponsive material in a skin region when the housing is positioned adjacent to the skin region. A controllable optical system is mounted with respect to the housing and the light source such that light from the light source may be focused on a skin region by the controllable optical system when the housing is positioned relative to the skin region at step 1356. At step 1358, driver interface circuitry is connected to the light source and the controllable optical system, the driver interface circuitry adapted to receive one or more control signals from a microprocessor-based controller and responsive to the control signals to drive the controllable optical system and the light source to focus light on one or more locations in the skin region according to a pattern. At step 1360, software code is provided that is executable by the microprocessor based controller to generate the one or more control signals. In some embodiments, the driver interface circuitry may be adapted to receive the one or more control signals from a microprocessor-based controller. In some embodiments, the method may include providing software code executable by the microprocessor-based controller to generate the one or more control signals.

Figure 33:
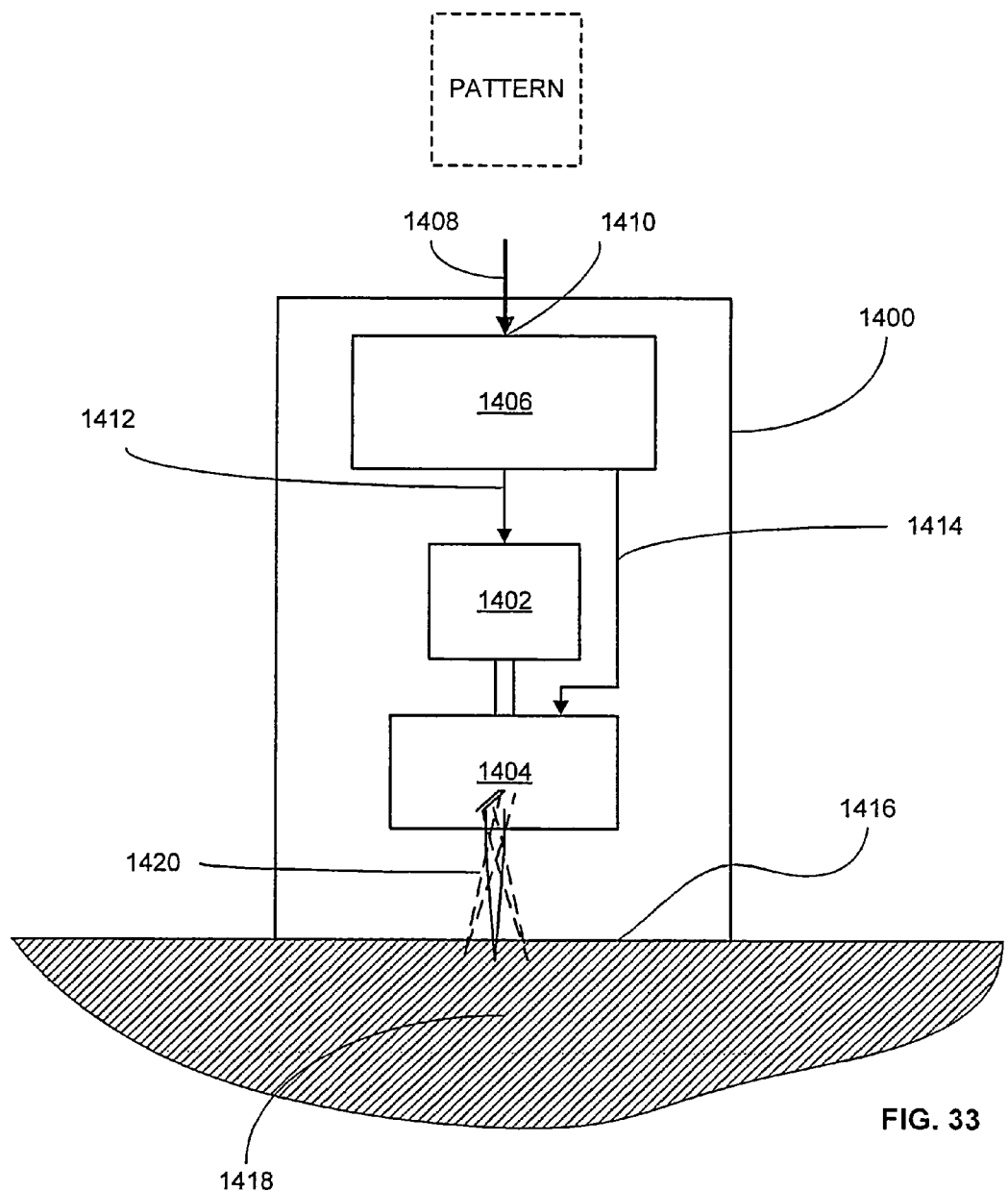
FIG. 33 is a block diagram of a system for delivery of patterned light.

FIG. 33 depicts features of a device as described in connection with FIG. 32; included are housing 1400, light source 1402, controllable optical system 1404, and driver interface circuitry 1406. Driver interface circuitry receives at least one control signal 1408 on input 1410, and generates control signals 1412 and 1414 for driving light source 1402 and controllable optical system 1404, respectively. Portion 1416 of housing 1400 may be configured to be positioned adjacent a skin region 1418, so that light 1420 may be directed to skin region 1418 by controllable optical system 1404.

The methods, apparatuses, and approaches described herein may be modified and combined in a variety of ways analogous to those of photolithography of silicon wafers. For example, masks or stencils may be used to form positive or negative patterns. Additive and subtractive processing may be performed by appropriate combinations of steps. For example, multiple steps, each involving the use of a different stencil and a different depth of focus of light in the skin, may be used to form a patterned distribution of material that varies as a function of depth within the skin. As another example, a multi-step process may be used in which a material modified at a first step, for example by treatment at a first wavelength, may in turn influence (e.g. by causing, preventing, promoting, or inhibiting) a further reaction or modification of the same or a different material produced at a second step by treatment with a second wavelength. It will appreciated that a wide variety of combination of treatment steps may be devised to control formation of patterned distributions of material in skin. As with photolithography methods, as multiple steps involving patterned delivery of materials or light to the skin are used, it may be necessary to maintain alignment or registration of patterns delivered at each step, e.g. by controlling mask positioning or targeting of light or delivery of photoresponsive material. Methods of maintaining positioning, targeting, or alignment are known to those of skill in the art, and variations are considered to fall within the scope of the present invention.

With regard to the hardware and/or software used in the control of skin treatment systems according to the present embodiments, and particularly to the sensing, analysis, and control aspects of such systems, those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency or implementation convenience tradeoffs. Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. For example, those skilled in the art will recognize that optical aspects of implementations will require optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be implicitly understood by those with skill in the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the capabilities of one of skill in the art in light of this disclosure. In addition, those skilled in the art will appreciate that certain mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., links carrying packetized data).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices for detection or sensing, signal processing, and device control in the fashion set forth herein, and thereafter use standard engineering practices to integrate such described devices and/or processes into skin treatment systems as exemplified herein. That is, at least a portion of the devices and/or processes described herein can be integrated into a skin treatment system via a reasonable amount of experimentation.

Those having skill in the art will recognize that systems as described herein may include one or more of a memory such as volatile and non-volatile memory, processors such as microprocessors and digital signal processors, computational-supporting or -associated entities such as operating systems, user interfaces, drivers, sensors, actuators, applications programs, one or more interaction devices, such as data ports, control systems including feedback loops and control implementing actuators (e.g., devices for sensing position and/or velocity and/or acceleration or time-rate-of-change thereof; control motors for moving and/or adjusting components). A skin treatment system may be implemented utilizing any suitable available components, combined with standard engineering practices.

The foregoing-described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

Although the methods, devices, systems and approaches herein have been described with reference to certain preferred embodiments, other embodiments are possible. As illustrated by the foregoing examples, various choices of light delivery system configuration and method of delivery of photoresponsive material may be within the scope of the invention. As has been discussed, the choice of system configuration may depend on the intended application of the system, the environment in which the system is used, cost, personal preference or other factors. System design, manufacture, and control processes may be modified to take into account choices of photoresponsive material and intended application, and such modifications, as known to those of skill in the arts of display design and construction, may fall within the scope of the invention. Therefore, the full spirit or scope of the invention is defined by the appended claims and is not to be limited to the specific embodiments described herein.

The invention claimed is:

1. A method of producing a patterned distribution of a material within a skin region, comprising:
    delivering a photoresponsive material to a skin region of a subject in a first pattern; and
    delivering targeted light to the skin region in a second pattern, said second pattern overlapping partially with said first pattern, wherein photoresponsive material in the areas of overlap between said first pattern and said second pattern undergoes photomodification to form an overlap pattern of modified photoresponsive material within said skin region.

2. The method of claim 1, wherein delivering the photoresponsive material to the skin region includes topically delivering the photoresponsive material to the skin region.

3. The method of claim 1, wherein delivering the photoresponsive material to the skin region includes injecting the photoresponsive material into the skin region.

4. The method of claim 1, including delivering targeted light to said skin region in said second pattern by delivering targeted light to a plurality of locations in said skin region according to said second pattern.

5. The method of claim 4, including delivering targeted light to said plurality of locations by delivering targeted light to said plurality of locations under software control.

6. The method of claim 4, including delivering targeted light to said plurality of locations by delivering targeted light to said plurality of locations under microprocessor control.

7. The method of claim 1, wherein delivering targeted light to said skin region in said second pattern includes delivering targeted light to said skin region according to a decorative pattern.

8. The method of claim 1, wherein delivering targeted light to said skin region in said second pattern includes delivering targeted light to said skin region according to a pattern corresponding to one or more structures in said skin region.

9. The method of claim 2, including topically delivering said photoresponsive material to said skin region in the form of an aerosol, cream, emulsion, gel, liquid, fluid, gas, vapor, lotion, patch, powder, or combination thereof.

10. The method of claim 3, including delivering said photoresponsive material to said skin region by injecting said photoresponsive material below the stratum corneum of said skin region with the use of a microneedle array.

11. The method of claim 1, wherein said modified photoresponsive material is visible under natural light.

12. The method of claim 1, wherein said modified photoresponsive material is visible under ultraviolet light.

13. The method of claim 1, wherein said modified photoresponsive material is fluorescent.

14. The method of claim 1, wherein said modified photoresponsive material is a pigment, dye, pharmaceutical compound, or cosmetic material.

15. The method of claim 1, wherein delivering targeted light to said skin region includes delivering targeted light having wavelength content, time-averaged flux and/or fluence sufficient to cause a photo cross-linking reaction of said photoresponsive material.

16. The method of claim 1, wherein delivering targeted light to said skin region includes delivering targeted light having wavelength content, time-averaged flux and/or fluence sufficient to cause a photochromic reaction of said photoresponsive material.

17. The method of claim 1, wherein delivering targeted light to said skin region includes delivering targeted light having wavelength content, time-averaged flux and/or fluence sufficient to cause a photodimerization reaction or other photopolymerization reaction of said photoresponsive material.

18. The method of claim 1, wherein delivering said photoresponsive material to said skin region of a subject includes delivering a photochromic material.

19. The method of claim 1, wherein delivering said photoresponsive material to said skin region of a subject includes delivering a photodynamic therapy agent.

* * * * *

UNITED STATES PATENT AND TRADEMARK OFFICE
CERTIFICATE OF CORRECTION

| | | |
|---|---|---|
| PATENT NO. | : 8,562,657 B2 | Page 1 of 1 |
| APPLICATION NO. | : 12/005709 | |
| DATED | : October 22, 2013 | |
| INVENTOR(S) | : Bran Ferren et al. | |

It is certified that error appears in the above-identified patent and that said Letters Patent is hereby corrected as shown below:

On the Title Page

Item (75) the residence of inventor -Nathan P. Myhrvold, Median, WA- is misspelled, and should read as follows:

--Nathan P. Myhrvold, Medina, WA--

Signed and Sealed this
Thirty-first Day of December, 2013

Margaret A. Focarino
*Commissioner for Patents of the United States Patent and Trademark Office*